US012696919B2

(12) United States Patent
Boesen et al.

(10) Patent No.: US 12,696,919 B2
(45) Date of Patent: Aug. 4, 2026

(54) CANNABINOID LIPID PREMIXTURE

(71) Applicant: Fertin Pharma A/S, Vejle (DK)

(72) Inventors: Dorthe Schackinger Boesen, Vejle (DK); Simon Lykke Roest Laursen, Aarhus N (DK); Sanne Skov Jensen, Fredericia (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 19/201,518

(22) Filed: May 7, 2025

(65) Prior Publication Data

US 2025/0261675 A1      Aug. 21, 2025

Related U.S. Application Data

(63) Continuation of application No. 17/857,937, filed on Jul. 5, 2022.

(51) Int. Cl.
| | |
|---|---|
| *A23L 29/00* | (2016.01) |
| *A23L 27/30* | (2016.01) |
| *A23L 29/30* | (2016.01) |
| *A23L 33/105* | (2016.01) |
| *A61K 36/185* | (2006.01) |

(52) U.S. Cl.
CPC ............. *A23L 29/035* (2016.08); *A23L 27/34* (2016.08); *A23L 29/37* (2016.08); *A23L 33/105* (2016.08); *A61K 36/3482* (2024.05)

(58) Field of Classification Search
CPC .................................................. A61K 31/658
See application file for complete search history.

(56) References Cited

U.S. PATENT DOCUMENTS

| | | | |
|---|---|---|---|
| 5,587,179 | A | 12/1996 | Gergely et al. |
| 2011/0136883 | A1 | 6/2011 | Injac et al. |
| 2019/0015383 | A1 | 1/2019 | Woelfel et al. |
| 2020/0330423 | A1* | 10/2020 | Brunn .................. A61K 9/0056 |

| | | | |
|---|---|---|---|
| 2021/0212946 | A1 | 7/2021 | Friedman |
| 2021/0267933 | A1 | 9/2021 | Bruun et al. |
| 2021/0353589 | A1* | 11/2021 | Levy ...................... A61K 31/01 |
| 2021/0393522 | A1 | 12/2021 | Chavan |
| 2022/0331266 | A1 | 10/2022 | Mills et al. |
| 2022/0339227 | A1 | 10/2022 | Williams, III et al. |
| 2022/0347118 | A1 | 11/2022 | Ristevski et al. |
| 2023/0030491 | A1 | 2/2023 | Zhou et al. |
| 2023/0157963 | A1 | 5/2023 | Moaseri et al. |
| 2023/0210771 | A1 | 7/2023 | Sloat et al. |
| 2023/0310465 | A1 | 10/2023 | Kocherlakota et al. |
| 2023/0355523 | A1 | 11/2023 | Karolchyk |
| 2023/0364026 | A1 | 11/2023 | Selvaraj et al. |
| 2023/0414518 | A1 | 12/2023 | Mileto et al. |
| 2024/0002358 | A1 | 1/2024 | Meckler et al. |
| 2024/0008514 | A1 | 1/2024 | Boesen et al. |
| 2024/0050450 | A1 | 2/2024 | Ogburn et al. |
| 2024/0082157 | A1 | 3/2024 | Macleod |
| 2024/0139216 | A1 | 5/2024 | Ristevski et al. |
| 2024/0325414 | A1 | 10/2024 | Alderman et al. |

FOREIGN PATENT DOCUMENTS

| | | | |
|---|---|---|---|
| CA | 3040513 | A1 | 10/2020 |
| EP | 2953617 | A1 | 12/2015 |
| WO | 2020211912 | A1 | 10/2020 |
| WO | 2020211913 | A1 | 10/2020 |
| WO | 2021119844 | A1 | 6/2021 |

OTHER PUBLICATIONS

Written Opinion and International Search Report for Application No. PCT/DK2023/050179 dated Oct. 17, 2023.

* cited by examiner

*Primary Examiner* — Michele L Jacobson
(74) *Attorney, Agent, or Firm* — Harris Beach Murtha Cullina PLLC

(57) ABSTRACT
The invention relates to a powder premixture for oral administration of cannabinoids, comprising a cannabinoid powder composition comprising one or more isolated cannabinoids in an amount of at least 2% by weight of the powder premixture; a lipid composition comprising one or more triglycerides in an amount of at least 1.0% by weight of the powder premixture; and a sweetener powder composition comprising one or more sweeteners, wherein the weight ratio between the one or more triglycerides and the one or more sweeteners is in the range of 1:50 to 1:4.

22 Claims, No Drawings

CANNABINOID LIPID PREMIXTURE

FIELD OF THE INVENTION

The invention relates to the field of cannabinoids. In particular, the invention relates to a powder premixture for oral administration of cannabinoids.

BACKGROUND OF THE INVENTION

Cannabinoids are a group of chemicals found in *Cannabis sativa, Cannabis indica, Cannabis ruderalis*, Marijuana plant and related plant species. They are known to activate cannabinoid receptors (CB1 and CB2). These chemicals are also produced endogenously in humans and other animals. Cannabinoids are cyclic molecules exhibiting particular properties such as being lipophilic, have the ability to easily cross the blood-brain barrier, and having low toxicity.

*Cannabis sativa* contains more than 400 chemicals and approximately 120 cannabinoids, the active constituents of *cannabis*, including tetrahydrocannabinol (THC), cannabidiol (CBD), cannabinol (CBN), tetrahydrocannabivarin (THCV) and cannabigerol (CBG). Pharmacologically, the principal psychoactive constituent of *cannabis* is tetrahydrocannabinol (THC), which is used for treating a wide range of medical conditions, including glaucoma, AIDS wasting, neuropathic pain, treatment of spasticity associated with multiple sclerosis, fibromyalgia, and chemotherapy-induced nausea. THC is also effective in the treatment of allergies, inflammation, infection, depression, migraine, bipolar disorders, anxiety disorder, drug dependency and drug withdrawal syndromes.

Oral administration of cannabinoids is a common route of administration. Cannabinoids are highly lipophilic, meaning that they are soluble in lipids and some organic solvents while being substantially insoluble or only sparsely soluble in water. Cannabinoids are soluble in highly non-polar solvents. Some of these solvents are pharmaceutically unacceptable, and the pharmaceutically acceptable solvents need to be used in high concentrations to produce solutions.

Various solutions have been suggested in the prior art with respect to oral formulations for delivery of cannabinoids. Among these solutions, solid dosage forms, lozenges, chewing gums and pouches have been proposed. While these solutions may have certain benefits with respect to oral delivery of cannabinoids, such as CBD or THC, these solutions have been mainly focused on either release from the application forms or certain components that allow effective absorption of the cannabinoids in the mucosa.

Generally, less attention has been given to accurate dosing of cannabinoids and reliability of formulating cannabinoids, such as CBD or THC, in oral formulations. For instance, homogeneous products would be beneficial but to some degree have been counteracted by the nature of the cannabinoids being highly lipophilic and thereby potentially interacting with remaining components of the oral formulations.

It is a desire in the prior art with improved homogeneity but hitherto provided solutions have traditionally been considered less suitable also partly in view of the desire to provide fast releasing products. Already available means for providing improved homogeneity have shown to be associated with drawbacks while at the same time being required to provide fast release of the cannabinoids.

In formulating solid dosage forms, various challenges are associated with obtaining a homogenous mixture where variations are avoided and a safe and convenient delivery may be obtained. Also, the general formulation of the tablets offering convenience to the user need not be compromised which is often the case if conventional delivery means are applied.

Furthermore, it is preferable that a formulation is provided that may also help in obtaining improved sensorics properties of oral cannabinoid delivery. Here, important sensorics properties include friability, texture, flavor perception, sweetness perception and off-notes associated with cannabinoids. These properties are both relevant from a convenience perspective in solid dosage forms, but certainly also in order to support an appropriate delivery of cannabinoids from the tablets and avoid adverse side effects of cannabinoids.

Another challenge is that cannabinoids tend to be associated with off-notes during administration due to the specific physiochemical properties of the compounds. The taste masking challenge is more profound when a higher release of cannabinoids are delivered. If off-notes are the predominant sensation during administration, convenience may be affected and even more critically, the delivery of cannabinoids may also be affected.

Hence, there is a need in the prior art for powders and formulations that solve the above-referenced challenges and problems of the prior art. In particular, there is a need in the prior art for powders to be applied in various administration form, such as tablets, pouches, chewing gums and lozenges, that are both associated with a suitable uniformity of content of the cannabinoids and offer suitable sensorial properties. More particularly, it is a desire that these formulations are also acceptable or improved with respect to taste masking and give a desired release during administration.

SUMMARY OF THE INVENTION

Accordingly, there is provided a powder premixture for oral administration of cannabinoids, comprising a cannabinoid powder composition comprising one or more isolated cannabinoids in an amount of at least 2% by weight of the powder premixture; a lipid composition comprising one or more triglycerides in an amount of at least 1.0% by weight of the powder premixture; and a sweetener powder composition comprising one or more sweeteners, wherein the weight ratio between the one or more triglycerides and the one or more sweeteners is in the range of 1:50 to 1:4.

In another aspect of the invention, there is provided oral administration forms where this powder is incorporated, such as partly or completely.

In yet another aspect, there is provided methods for preparing powder premixtures for oral administration of cannabinoids.

One of the advantages of the present invention is that accurate dosing of cannabinoids and reliability of formulating cannabinoids, such as CBD or THC, in oral formulations may be provided. For instance, homogeneous products would be beneficial but to some degree have been counteracted by the nature of the cannabinoids being highly lipophilic and thereby potentially interacting with remaining components of the oral formulations.

Traditionally, hitherto provided solutions have been considered less suitable also partly in view of the desire to provide fast releasing products. Already available means for providing improved homogeneity have shown to be associated with drawbacks while at the same time being required to provide fast release of the cannabinoids.

One prejudice in the prior art is that cannabinoids being highly lipophilic may not be properly formulated with other components in a powder or solid dosage form without compromising the other components and the interacting in the system.

Another advantage is that the formulation according to the invention may also help in obtaining improved sensorics properties of oral cannabinoid delivery. Here, important sensorics properties include friability, texture, flavor perception, sweetness perception and off-notes associated with cannabinoids. These properties are both relevant from a convenience perspective in solid dosage forms, but certainly also in order to support an appropriate delivery of cannabinoids from the solid dosage forms and avoid adverse side effects of cannabinoids.

Yet another advantage is that the invention may help addressing off-notes during administration. The taste masking challenge is more profound when a higher release of cannabinoids is delivered by such solid dosage forms. If off-notes are the predominant sensation during administration, convenience may be affected and even more critically, the delivery of cannabinoids may also be affected.

In terms of improved content of uniformity, surprisingly results were seen. Generally, the method used for content uniformity of samples is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity, e.g. employing standard HPLC techniques.

When attempting to obtain a high degree of even distribution, insufficient mixing may lead to uneven distribution, such as undesirable agglomeration of particles within certain parts of the solid dosage form. Also, even if mixing very thoroughly the ingredients, an undesirable handling of the mixture from the mixing to a tableting machine may lead to segregation. For example, smaller particles may typically segregate to the bottom part of a container, thereby leading to different particle distributions for different solid dosage forms. Particularly when the different ingredients have different particle sizes, segregation may lead to different contents in different solid dosage forms.

Compared to powders where the lipid composition according to the invention was not applied in a formulation with a cannabinoid powder composition, content of uniformity was inferior. This was highly surprising to the inventors of the instant invention and was not expected in view of the prior art attempts to provide suitable solutions.

In some embodiments of the invention, a series of at least 5 samples each having the same fixed weight in the range of 0.25-2 g and taken from the powder mixture to be analyzed varies with a relative standard deviation (RSD) below 10% with respect to the content of the one or more cannabinoids.

In some embodiments of the invention, a series of at least 5 samples each having the same fixed weight in the range of 0.25-2 g and taken from the powder mixture to be analyzed varies with a relative standard deviation (RSD) below 5% with respect to the content of the one or more cannabinoids.

In some embodiments of the invention, a series of at least 5 samples each having the same fixed weight in the range of 0.25-2 g and taken from the powder mixture to be analyzed varies with a relative standard deviation (RSD) below 2% with respect to the content of the one or more cannabinoids.

In some embodiments of the invention, the weight ratio between the one or more triglycerides and the one or more sweeteners is in the range of 1:50 to 1:5. In some embodiments of the invention, the weight ratio between the one or more triglycerides and the one or more sweeteners is in the range of 1:50 to 1:7.

In some embodiments of the invention, the weight ratio between the one or more triglycerides and the one or more sweeteners is in the range of 1:50 to 1:10. In some embodiments of the invention, the weight ratio between the one or more triglycerides and the one or more sweeteners is in the range of 1:50 to 1:7. In some embodiments of the invention, the weight ratio between the one or more triglycerides and the one or more sweeteners is in the range of 1:50 to 1:5.

In some embodiments of the invention, the weight ratio between the one or more triglycerides and the one or more sweeteners is in the range of 1:40 to 1:10. In some embodiments of the invention, the weight ratio between the one or more triglycerides and the one or more sweeteners is in the range of 1:40 to 1:12. In some embodiments of the invention, the weight ratio between the one or more triglycerides and the one or more sweeteners is in the range of 1:40 to 1:15. In some embodiments of the invention, the weight ratio between the one or more triglycerides and the one or more sweeteners is in the range of 1:40 to 1:20.

In some embodiments of the invention, the one or more triglycerides is of vegetable origin. In some embodiments of the invention, the one or more triglycerides is free of triglycerides of animal origin.

In some embodiments of the invention, the one or more triglycerides is selected from one or more C4 to C14 triglycerides. In some embodiments of the invention, the one or more triglycerides is selected from one or more C4 to C12 triglycerides. In some embodiments of the invention, the one or more triglycerides is selected from one or more C6 to C14 triglycerides. In some embodiments of the invention, the one or more triglycerides is selected from one or more C6 to C12 triglycerides. In some embodiments of the invention, the one or more triglycerides is selected from one or more C6 to C10 triglycerides. In some embodiments of the invention, the one or more triglycerides is selected from one or more C8 to C12 triglycerides. In some embodiments of the invention, the one or more triglycerides is selected from one or more C8 to C10 triglycerides.

In some embodiments of the invention, the one or more triglycerides comprises a partially hydrogenated vegetable oil. In some embodiments of the invention, the one or more triglycerides comprises a fully hydrogenated vegetable oil (HVO).

In some embodiments of the invention, the one or more triglycerides is selected from triglycerides being liquid at or above 0 Degree Celsius.

In some embodiments of the invention, the one or more triglycerides is a blend of a number of triglycerides.

In some embodiments of the invention, the one or more triglycerides is heated to a temperature above ambient temperature before being added in the premixture.

In some embodiments of the invention, the one or more triglycerides is heated to a temperature of 50 to 80 Degree Celsius before being added in the premixture. In some embodiments of the invention, the one or more triglycerides is heated to a temperature of 50 to 70 Degree Celsius before being added in the premixture. In some embodiments of the invention, the one or more triglycerides is heated to a temperature of 50 to 60 Degree Celsius before being added in the premixture. In some embodiments of the invention, the one or more triglycerides is heated to a temperature of 60 to 70 Degree Celsius before being added in the premixture. In some embodiments of the invention, the one or more triglycerides is heated to a temperature of 40 to 80 Degree Celsius before being added in the premixture. In some embodiments of the invention, the one or more triglycerides is heated to a temperature of 40 to 70 Degree Celsius before being added in the premixture.

In some embodiments of the invention, the one or more triglycerides is selected from triglycerides being liquid at or above 20 Degree Celsius. In some embodiments of the invention, the one or more triglycerides is selected from triglycerides being liquid at or above 25 Degree Celsius. In some embodiments of the invention, the one or more triglycerides is selected from triglycerides being liquid at or above 30 Degree Celsius. In some embodiments of the invention, the one or more triglycerides is selected from triglycerides being liquid at or above 40 Degree Celsius.

In some embodiments of the invention, the one or more triglycerides is selected from triglycerides with a melting temperature of 25 to 50 Degree Celsius. In some embodiments of the invention, the one or more triglycerides is selected from triglycerides with a melting temperature of 25 to 40 Degree Celsius. In some embodiments of the invention, the one or more triglycerides is selected from triglycerides with a melting temperature of 30 to 40 Degree Celsius. In some embodiments of the invention, the one or more triglycerides is selected from triglycerides with a melting temperature of 30 to 50 Degree Celsius.

In some embodiments of the invention, the one or more triglycerides comprises caprylic acid in an amount of 50 to 80% by weight. In some embodiments of the invention, the one or more triglycerides comprises caprylic acid in an amount of 50 to 70% by weight. In some embodiments of the invention, the one or more triglycerides comprises caprylic acid in an amount of 50 to 90% by weight. In some embodiments of the invention, the one or more triglycerides comprises caprylic acid in an amount of 60 to 90% by weight. In some embodiments of the invention, the one or more triglycerides comprises caprylic acid in an amount of 65 to 80% by weight.

In some embodiments of the invention, the one or more triglycerides comprises capric acid in an amount of 20 to 45% by weight. In some embodiments of the invention, the one or more triglycerides comprises capric acid in an amount of 20 to 50% by weight. In some embodiments of the invention, the one or more triglycerides comprises capric acid in an amount of 20 to 40% by weight. In some embodiments of the invention, the one or more triglycerides comprises capric acid in an amount of 20 to 35% by weight.

In some embodiments of the invention, the one or more triglycerides comprises capric acid in an amount of 25 to 50% by weight. In some embodiments of the invention, the one or more triglycerides comprises capric acid in an amount of 25 to 40% by weight. In some embodiments of the invention, the one or more triglycerides comprises capric acid in an amount of 30 to 50% by weight. In some embodiments of the invention, the one or more triglycerides comprises capric acid in an amount of 30 to 45% by weight. In some embodiments of the invention, the one or more triglycerides comprises capric acid in an amount of 20 to 30% by weight.

In some embodiments of the invention, the one or more triglycerides comprises caprylic acid in an amount of 65 to 80% by weight and capric acid in an amount of 20 to 35% by weight.

In some embodiments of the invention, the one or more triglycerides comprises caprylic acid in an amount of 50 to 65% by weight and capric acid in an amount of 30 to 45% by weight.

In some embodiments of the invention, the one or more triglycerides comprises coconut oil. In some embodiments of the invention, the one or more triglycerides is consisting essentially of coconut oil. In some embodiments of the invention, the one or more triglycerides is coconut oil.

In some embodiments of the invention, the one or more triglycerides is present in an amount of at least 1.5% by weight of the powder premixture.

In some embodiments of the invention, the one or more triglycerides is present in an amount of at least 2.0% by weight of the powder premixture.

In some embodiments of the invention, the one or more triglycerides is present in an amount of at least 2.5% by weight of the powder premixture.

In some embodiments of the invention, the one or more triglycerides is present in an amount of at least 3.0% by weight of the powder premixture.

In some embodiments of the invention, the one or more triglycerides is present in an amount of at least 4.0% by weight of the powder premixture.

In some embodiments of the invention, the one or more triglycerides is present in an amount of at least 5.0% by weight of the powder premixture. In some embodiments of the invention, the one or more triglycerides is present in an amount of at least 6.0% by weight of the powder premixture. In some embodiments of the invention, the one or more triglycerides is present in an amount of at least 7.0% by weight of the powder premixture. In some embodiments of the invention, the one or more triglycerides is present in an amount of at least 8.0% by weight of the powder premixture. In some embodiments of the invention, the one or more triglycerides is present in an amount of at least 9.0% by weight of the powder premixture. In some embodiments of the invention, the one or more triglycerides is present in an amount of at least 10.0% by weight of the powder premixture.

In some embodiments of the invention, the one or more sweeteners is present in an amount of at least 50% by weight of the powder premixture.

In some embodiments of the invention, the one or more sweeteners is present in an amount of at least 60% by weight of the powder premixture.

In some embodiments of the invention, the one or more sweeteners is present in an amount of at least 70% by weight of the powder premixture.

In some embodiments of the invention, the one or more sweeteners is present in an amount of at least 75% by weight of the powder premixture.

In some embodiments of the invention, the one or more sweeteners is present in an amount of at least 80% by weight of the powder premixture. In some embodiments of the invention, the one or more sweeteners is present in an amount of at least 90% by weight of the powder premixture. In some embodiments of the invention, the one or more sweeteners is present in an amount of at least 95% by weight of the powder premixture.

In some embodiments of the invention, the one or more sweeteners is selected from the group consisting of saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, and the like, alone or in combination. These sugar sweeteners may also be included as a humectant.

In some embodiments of the invention, the one or more sweeteners comprises dextrose. In some embodiments of the invention, the one or more sweeteners is dextrose.

In some embodiments of the invention, the one or more sweeteners comprises dextrin. In some embodiments of the invention, the one or more sweeteners is dextrin.

In some embodiments of the invention, the one or more sweeteners comprises sucrose. In some embodiments of the invention, the one or more sweeteners is sucrose.

In some embodiments of the invention, the one or more sweeteners comprises fructose. In some embodiments of the invention, the one or more sweeteners is fructose.

In some embodiments of the invention, the one or more sweeteners comprises one or more sugar alcohols.

In some embodiments of the invention, the one or more sugar alcohols is selected from the group consisting of sorbitol, xylitol, maltitol, isomalt, mannitol, erythritol, lactitol, and combinations thereof.

In some embodiments of the invention, the one or more sugar alcohols is selected from the group consisting of xylitol, erythritol, maltitol, mannitol, and combinations thereof.

In some embodiments of the invention, the one or more sugar alcohols comprises xylitol. In some embodiments of the invention, the one or more sugar alcohols is xylitol.

In some embodiments of the invention, the one or more sugar alcohols comprises erythritol. In some embodiments of the invention, the one or more sugar alcohols is erythritol.

In some embodiments of the invention, the one or more sugar alcohols comprises mannitol. In some embodiments of the invention, the one or more sugar alcohols is mannitol.

In some embodiments of the invention, the one or more sugar alcohols comprises maltitol. In some embodiments of the invention, the one or more sugar alcohols is maltitol.

In some embodiments of the invention, the one or more sugar alcohols comprises granulated sugar alcohol particles.

In some embodiments of the invention, the one or more sugar alcohols comprises non-directly (non-DC) sugar alcohol particles.

In some embodiments of the invention, the one or more sweeteners comprises one or more saccharides.

In some embodiments of the invention, the one or more sweeteners comprises at least two types of sweetener particles.

In some embodiments of the invention, the one or more sweeteners comprises sweetener particles having a particle size with more than 50% of the particles being below 250 microns. In some embodiments of the invention, the one or more sweeteners comprises sweetener particles having a particle size with more than 60% of the particles being below 250 microns. In some embodiments of the invention, the one or more sweeteners comprises sweetener particles having a particle size with more than 70% of the particles being below 250 microns. In some embodiments of the invention, the one or more sweeteners comprises sweetener particles having a particle size with more than 80% of the particles being below 250 microns.

In some embodiments of the invention, the one or more sweeteners comprises sweetener particles having a particle size with more than 20% of the particles being above 500 microns. In some embodiments of the invention, the one or more sweeteners comprises sweetener particles having a particle size with more than 30% of the particles being above 500 microns. In some embodiments of the invention, the one or more sweeteners comprises sweetener particles having a particle size with more than 50% of the particles being above 500 microns.

In some embodiments of the invention, the weight ratio between the one or more triglycerides and the one or more isolated cannabinoids is in the range of 1:40 to 1:1. In some embodiments of the invention, the weight ratio between the one or more triglycerides and the one or more isolated cannabinoids is in the range of 1:30 to 1:1. In some embodiments of the invention, the weight ratio between the one or more triglycerides and the one or more isolated cannabinoids is in the range of 1:20 to 1:1. In some embodiments of the invention, the weight ratio between the one or more triglycerides and the one or more isolated cannabinoids is in the range of 1:15 to 1:1.

In some embodiments of the invention, the weight ratio between the one or more triglycerides and the one or more isolated cannabinoids is in the range of 1:10 to 1:1. In some embodiments of the invention, the weight ratio between the one or more triglycerides and the one or more isolated cannabinoids is in the range of 1:10 to 1:2. In some embodiments of the invention, the weight ratio between the one or more triglycerides and the one or more isolated cannabinoids is in the range of 1:8 to 1:2. In some embodiments of the invention, the weight ratio between the one or more triglycerides and the one or more isolated cannabinoids is in the range of 1:7 to 1:2. In some embodiments of the invention, the weight ratio between the one or more triglycerides and the one or more isolated cannabinoids is in the range of 1:6 to 1:2. In some embodiments of the invention, the weight ratio between the one or more triglycerides and the one or more isolated cannabinoids is in the range of 1:5 to 1:2.

In some embodiments of the invention, the one or more isolated cannabinoids is present in an amount of at least 5% by weight of the powder premixture. In some embodiments of the invention, the one or more isolated cannabinoids is present in an amount of at least 7% by weight of the powder premixture.

In some embodiments of the invention, the one or more isolated cannabinoids is present in an amount of at least 10% by weight of the powder premixture. In some embodiments of the invention, the one or more isolated cannabinoids is present in an amount of at least 15% by weight of the powder premixture.

In some embodiments of the invention, the one or more isolated cannabinoids is present in an amount of at least 20% by weight of the powder premixture. In some embodiments of the invention, the one or more isolated cannabinoids is present in an amount of at least 25% by weight of the powder premixture.

In some embodiments of the invention, the one or more isolated cannabinoids is present in an amount of at least 30% by weight of the powder premixture. In some embodiments of the invention, the one or more isolated cannabinoids is present in an amount of at least 35% by weight of the powder premixture. In some embodiments of the invention, the one or more isolated cannabinoids is present in an amount of at least 40% by weight of the powder premixture.

In some embodiments of the invention, the one or more isolated cannabinoids is present in the powder mixture in an amount of 0.1 to 400 mg. In some embodiments of the invention, the one or more isolated cannabinoids is present in the powder mixture in an amount of 0.1 to 300 mg. In some embodiments of the invention, the one or more isolated cannabinoids is present in the powder mixture in an amount of 0.1 to 250 mg.

In some embodiments of the invention, the one or more isolated cannabinoids is present in the powder premixture in an amount of 1 to 200 mg. In some embodiments of the invention, the one or more isolated cannabinoids is present in the powder premixture in an amount of 1 to 150 mg. In some embodiments of the invention, the one or more isolated cannabinoids is present in the powder premixture in an amount of 1 to 100 mg.

In some embodiments of the invention, the one or more isolated cannabinoids is present in the powder premixture in an amount of 5 to 200 mg. In some embodiments of the invention, the one or more isolated cannabinoids is present in the powder premixture in an amount of 5 to 100 mg.

In some embodiments of the invention, the one or more isolated cannabinoids is present in the powder premixture in an amount of 3 to 200 mg. In some embodiments of the invention, the one or more isolated cannabinoids is present in the powder premixture in an amount of 3 to 100 mg.

In some embodiments of the invention, the one or more isolated cannabinoids is present in the powder premixture in an amount of 2 to 200 mg. In some embodiments of the invention, the one or more isolated cannabinoids is present in the powder premixture in an amount of 2 to 100 mg.

In some embodiments of the invention, the one or more isolated cannabinoids is present in the powder premixture in an amount of 10 to 100 mg.

In some embodiments of the invention, the one or more isolated cannabinoids is selected from the group consisting of cannabidiol (CBD), cannabidiolic acid (CBDA), cannabidivarin (CBDV), and combinations thereof.

In some embodiments of the invention, the one or more isolated cannabinoids is selected from the group consisting of tetrahydrocannabinol (THC), tetrahydrocannabinolic acid (THCA), tetrahydrocannabivarin (THCV), and combinations thereof.

In some embodiments of the invention, the one or more isolated cannabinoids comprise cannabigerol (CBG).

In an embodiment of the invention, the one or more cannabinoids comprise cannabidiol (CBD), cannabidiolic acid (CBDA), cannabidivarin (CBDV), salts and derivatives thereof.

In an embodiment of the invention, the one or more cannabinoids comprise tetrahydrocannabinol (THC), tetrahydrocannabinolic acid (THCA), tetrahydrocannabivarin (THCV), salts and derivatives thereof.

In an embodiment of the invention, the one or more cannabinoids comprise cannabigerol (CBG), salts and derivatives thereof.

In some embodiments of the invention, the cannabinoid is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabinol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof, derivatives thereof and mixtures of cannabinoids.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises CBD. In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean (−)-trans-$\Delta^9$-tetrahydrocannabinol, i.e. (6aR,10aR)-delta-9-tetrahydrocannabinol). In an embodiment of the invention said one or more cannabinoids is THC.

In an embodiment of the invention, wherein the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In some embodiments of the invention, the one or more isolated cannabinoids is present in a purity of at least 90% (w/w).

In some embodiments of the invention, the one or more isolated cannabinoids is present in a purity of at least 95% (w/w).

In some embodiments of the invention, the one or more isolated cannabinoids is present in a purity of at least 98% (w/w).

In some embodiments of the invention, the one or more isolated cannabinoids does not include cannabinoid distillates.

In some embodiments of the invention, the one or more isolated cannabinoids does not include cannabinoid extracts.

In some embodiments of the invention, the one or more isolated cannabinoids does not include one or more isolated cannabinoids in a purity of less than 90% (w/w).

In some embodiments of the invention, the one or more isolated cannabinoids is dissolved in the one or more triglycerides before admixture with the sweetener powder composition.

In some embodiments of the invention, the one or more isolated cannabinoids is added in the sweetener powder composition before admixture with the one or more triglycerides.

In some embodiments of the invention, the one or more triglycerides is added in the sweetener powder composition before admixture with the one or more isolated cannabinoids.

In some embodiments of the invention, further ingredients are added in the premixture.

Generally, when it is mentioned that further ingredients are "added in the premixture" or similar wordings, the intended meaning is that these ingredients are added to the total mixture. Hence, the premixture could also be added to the further ingredients depending on the procedure and amounts involved. Usually, a "premix" or "premixture" are expressions used interchangeably. Further ingredients combined with the premixture is usually denoted a "powder blend" or similar wordings. The "powder blend" may comprise further ingredients.

In some embodiments of the invention, further ingredients are added in the premixture or in the powder blend selected from the group consisting of flavors, dry-binders, tableting aids, anti-caking agents, surfactants, emulsifiers, antioxidants, enhancers, mucoadhesives, absorption enhancers, high intensity sweeteners, softeners, colors, further active ingredients, water-soluble indigestible polysaccharides, water-insoluble polysaccharides, and any combination thereof.

In some embodiments of the invention, one or more flavoring agents is added in the premixture or powder blend.

In some embodiments of the invention, a high intensity sweetener is added in the premixture or powder blend.

In some embodiments of the invention, the premixture is a ready-to-use premixture.

In some embodiments of the invention, the premixture is to be applied in an amount of 10-99.9% by weight in combination with further ingredients In an aspect of the invention, a solid dosage form for oral administration of cannabinoids is provided comprising a premixture according to the invention.

In some embodiments of the invention, the premixture is present in an amount of 10-100% by weight of the solid dosage form. In some embodiments of the invention, the premixture is present in an amount of about 100% by weight of the solid dosage form. In some embodiments of the invention, the premixture is present in an amount of substantially 100% by weight of the solid dosage form. In some embodiments of the invention, the premixture is present in an amount of 10-90% by weight of the solid dosage form.

In some embodiments of the invention, the premixture is present in an amount of 15-75% by weight of the solid dosage form. In some embodiments of the invention, the premixture is present in an amount of 20-70% by weight of the solid dosage form. In some embodiments of the invention, the premixture is present in an amount of 25-60% by weight of the solid dosage form. In some embodiments of the invention, the premixture is present in an amount of 30-50% by weight of the solid dosage form.

In some embodiments of the invention, a series of at least 10 solid dosage forms comprise the one or more cannabinoids in an amount varying with a relative standard deviation (RSD) below 5%.

Generally, the method used for content uniformity of samples is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 solid dosage forms comprise the one or more cannabinoids in an amount varying with a relative standard deviation (RSD) below 2%.

In an aspect of the invention, a tablet for oral administration of cannabinoids is provided comprising a premixture according to the invention.

In some embodiments of the invention, the premixture is present in an amount of 10-100% by weight of the tablet.

In some embodiments of the invention, the premixture is present in an amount of 15-75% by weight of the tablet.

In some embodiments of the invention, the tablet comprises one or more sugar alcohols in addition to the one or more sweeteners in the premixture selected from the group consisting of sorbitol, erythritol, maltitol, xylitol, isomalt, lactitol, mannitol, and combinations thereof.

In some embodiments of the invention, the tablet comprises one or more sweeteners in addition to the one or more sweeteners in the premixture in an amount of 20 to 80% by weight of the tablet.

In some embodiments of the invention, a series of at least 10 tablets comprise the one or more active pharmaceutical ingredients in an amount varying with a relative standard deviation (RSD) below 5%.

Generally, the method used for content uniformity of tablets is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 tablets comprise the one or more cannabinoids in an amount varying with a relative standard deviation (RSD) below 2%.

In some embodiments of the invention, the tablet comprises directly compressible (DC) sugar alcohol particles and non-directly compressible (non-DC) sugar alcohol particles.

In some embodiments of the invention, the tablet has a weight ratio between said non-DC sugar alcohol particles and said DC sugar alcohol particles, which is between 0.2 and 1.2.

In some embodiments of the invention, the tablet has a weight ratio between said non-DC sugar alcohol particles and said DC sugar alcohol particles, which is between 0.3 and 0.7.

In some embodiments of the invention, the tablet comprises one or more insoluble components selected from the group consisting of silica, microcrystalline cellulose, cellulose, silicified microcrystalline cellulose, clay, talc, starch, pregelatinized starch, calcium carbonate, dicalcium phosphate, magnesium carbonate, magnesium-alumino-metasilicates, hyper porous silica, and mixtures thereof.

In some embodiments of the invention, the tablet comprises one or more binders in an amount of 0.1 to 6% by weight of the tablet.

In some embodiments of the invention, the tablet comprises at least two modules, and wherein the premixture is comprised in at least one module of the tablet.

In some embodiments of the invention, the tablet comprises further ingredients selected from the group consisting of flavors, dry-binders, tableting aids, anti-caking agents, surfactants, emulsifiers, antioxidants, enhancers, mucoadhesives, absorption enhancers, high intensity sweeteners, softeners, colors, further active ingredients, water-soluble indigestible polysaccharides, water-insoluble polysaccharides, and any combination thereof.

In an aspect of the invention, a chewing gum for oral administration of cannabinoids is provided comprising a premixture according to the invention.

In some embodiments of the invention, the premixture is present in an amount of 15-75% by weight of the chewing gum.

In some embodiments of the invention, a series of at least 10 chewing gums comprise the one or more cannabinoids in an amount varying with a relative standard deviation (RSD) below 5%.

Generally, the method used for content uniformity of cannabinoids in chewing gums is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 chewing gums comprise the one or more cannabinoids in an amount varying with a relative standard deviation (RSD) below 2%.

In some embodiments of the invention, the chewing gum comprises gum base in an amount of 20-40% by weight of the chewing gum, and wherein the chewing gum is designed to be masticated into a coherent residual containing water-insoluble components.

In some embodiments of the invention, the chewing gum comprises gum base, and wherein the gum base comprises an elastomer selected from the group consisting of styrene-butadiene rubber (SBR), butyl rubber, polyisobutylene (PIB), and combinations thereof.

In some embodiments of the invention, the chewing gum comprises gum base, and wherein the gum base comprises at least 5% by weight of elastomer.

In some embodiments of the invention, the chewing gum comprises gum base, and wherein the gum base comprises gum base resins selected from natural resins and/or synthetic resins.

In some embodiments of the invention, the chewing gum comprises gum base, and wherein the gum base comprises at least 5% by weight of gum base resins.

In some embodiments of the invention, the chewing gum comprises gum base, and wherein the gum base comprises gum base particles having an average particle size of between 400 μm and 1400 μm.

In some embodiments of the invention, the chewing gum comprises one or more sugar alcohols in addition to the one or more sweeteners in the premixture selected from the group consisting of sorbitol, erythritol, maltitol, xylitol, isomalt, lactitol, mannitol, and combinations thereof.

In some embodiments of the invention, the chewing gum comprises one or more sweeteners in addition to the one or more sweeteners in the premixture in an amount of 20 to 60% by weight of the chewing gum.

In some embodiments of the invention, a series of at least 10 compressed chewing gums comprise the one or more cannabinoids in an amount varying with a relative standard deviation (RSD) below 5%.

Generally, the method used for content uniformity of cannabinoids in compressed chewing gums is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 compressed chewing gums comprise the one or more cannabinoids in an amount varying with a relative standard deviation (RSD) below 2%.

In some embodiments of the invention, the chewing gum comprises at least two compressed modules, and wherein the premixture is comprised in at least one of the two compressed modules.

In some embodiments of the invention, the chewing gum comprises at least two compressed modules, and wherein the two modules are different in composition.

In some embodiments of the invention, the chewing gum comprises at least two compressed modules, and wherein at least one of the two compressed modules does not comprise gum base.

In some embodiments of the invention, the chewing gum comprises further ingredients selected from the group consisting of flavors, dry-binders, tableting aids, anti-caking agents, surfactants, emulsifiers, antioxidants, enhancers, mucoadhesives, absorption enhancers, high intensity sweeteners, softeners, colors, further active ingredients, water-soluble indigestible polysaccharides, water-insoluble polysaccharides, and any combination thereof.

In an aspect of the invention, a lozenge for oral administration of cannabinoids is provided comprising a premixture according to the invention.

In some embodiments of the invention, the premixture is present in an amount of 10-100% by weight of the lozenge.

In some embodiments of the invention, the premixture is present in an amount of 15-75% by weight of the lozenge.

In some embodiments of the invention, a series of at least 10 lozenges comprise the one or more cannabinoids in an amount varying with a relative standard deviation (RSD) below 5%.

Generally, the method used for content uniformity of lozenges is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 lozenges comprise the one or more cannabinoids in an amount varying with a relative standard deviation (RSD) below 2%.

In some embodiments of the invention, the lozenge comprises one or more sugar alcohols in addition to the one or more sweeteners in the premixture selected from the group consisting of sorbitol, erythritol, maltitol, xylitol, isomalt, lactitol, mannitol, and combinations thereof.

In some embodiments of the invention, the lozenge comprises one or more sweeteners in addition to the one or more sweeteners in the premixture in an amount of 20 to 60% by weight of the lozenge.

In some embodiments of the invention, the lozenge comprises one or more insoluble components selected from the group consisting of silica, microcrystalline cellulose, cellulose, silicified microcrystalline cellulose, clay, talc, starch, pregelatinized starch, calcium carbonate, dicalcium phosphate, magnesium carbonate, magnesium-alumino-metasilicates, hyper porous silica, and mixtures thereof.

In some embodiments of the invention, the lozenge comprises one or more disintegrants operable to disintegrate the lozenge within a period of 1 minute or less in contact with oral saliva.

In some embodiments of the invention, the lozenge comprises one or more disintegrants selected from the group consisting of sodium croscarmellose, crospovidone, sodium starch glycolate, and combinations thereof.

In some embodiments of the invention, the lozenge comprises one or more disintegrants in an amount of 0.5 to 25% by weight of the lozenge.

In some embodiments of the invention, the lozenge comprises further ingredients selected from the group consisting of flavors, dry-binders, tableting aids, anti-caking agents, surfactants, emulsifiers, antioxidants, enhancers, mucoadhesives, absorption enhancers, high intensity sweeteners, softeners, colors, further active ingredients, water-soluble indigestible polysaccharides, water-insoluble polysaccharides, and any combination thereof.

In an aspect of the invention, a pouch for oral administration of cannabinoids is provided comprising a premixture according to the invention.

In some embodiments of the invention, the premixture is present in an amount of 10-100% by weight of the pouch.

In some embodiments of the invention, the premixture is present in an amount of 15-75% by weight of the pouch.

In some embodiments of the invention, a series of at least 10 pouches comprise the one or more cannabinoids in an amount varying with a relative standard deviation (RSD) below 5%.

Generally, the method used for content uniformity of pouches is determined according to European Pharmacopoeia 10.8 when using test method 2.9.40. Uniformity of dosage units. The acceptance value (AV) is calculated using mass variation (MV) or content uniformity (CU) depending on the dose and ratio of the drug substance. An appropriate analytical method is selected for content uniformity.

In some embodiments of the invention, a series of at least 10 pouches comprise the one or more cannabinoids in an amount varying with a relative standard deviation (RSD) below 2%.

In some embodiments of the invention, the pouch comprises one or more insoluble components selected from the group consisting of silica, clay, talc, starch, pregelatinized starch, calcium carbonate, dicalcium phosphate, magnesium carbonate, magnesium-alumino-metasilicates, hyper porous silica and mixtures thereof.

In some embodiments of the invention, the pouch comprises one or more insoluble fibres.

In some embodiments of the invention, the pouch comprises one or more insoluble fibres selected from wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bran fibers, bamboo fibers, powdered cellulose, microcrystalline cellulose and combinations thereof.

In some embodiments of the invention, the pouch comprises one or more sugar alcohols in addition to the one or more sweeteners in the premixture selected from the group consisting of sorbitol, erythritol, maltitol, xylitol, isomalt, lactitol, mannitol, and combinations thereof.

In some embodiments of the invention, the pouch comprises one or more sweeteners in addition to the one or more sweeteners in the premixture in an amount of 20 to 60% by weight of the pouch.

In some embodiments of the invention, the pouch comprises further ingredients selected from the group consisting of flavors, dry-binders, anti-caking agents, surfactants, emulsifiers, antioxidants, enhancers, mucoadhesives, absorption enhancers, high intensity sweeteners, softeners, colors, further active ingredients, water-soluble indigestible polysaccharides, water-insoluble polysaccharides, and any combination thereof.

In an aspect of the invention, there is provided a method of preparing a powder premixture for oral administration of cannabinoids, comprising the steps of:

i) dissolving or dispersing a cannabinoid powder composition comprising one or more isolated cannabinoids in a lipid composition comprising one or more triglycerides followed by ii) mixing a sweetener powder composition comprising one or more sweeteners with the mixture obtained in i) to obtain a powder premixture, wherein the weight ratio between the one or more triglycerides and the one or more sweeteners is in the range of 1:50 to 1:4.

In some embodiments of the invention, the one or more triglycerides is heated to a temperature above ambient temperature before being added in the premixture.

In an aspect of the invention, there is provided a powder premixture for oral administration of cannabinoids, comprising the steps of:

i) mixing a sweetener powder composition comprising one or more sweeteners with a cannabinoid powder composition comprising one or more isolated cannabinoids followed by ii) mixing a lipid composition comprising one or more triglycerides with the mixture obtained in i) to obtain a powder premixture, wherein the weight ratio between the one or more triglycerides and the one or more sweeteners is in the range of 1:50 to 1:4.

In some embodiments of the invention, the one or more triglycerides is heated to a temperature above ambient temperature before being added in the premixture.

In an aspect of the invention, there is provided a powder premixture for oral administration of cannabinoids, comprising the steps of:

i) mixing a sweetener powder composition comprising one or more sweeteners with a lipid composition comprising one or more triglycerides followed by ii) mixing a cannabinoid powder composition comprising one or more isolated cannabinoids with the mixture obtained in i) to obtain a powder premixture, wherein the weight ratio between the one or more triglycerides and the one or more sweeteners is in the range of 1:50 to 1:4.

In some embodiments of the invention, the one or more triglycerides is heated to a temperature above ambient temperature before being added in the premixture.

DETAILED DESCRIPTION OF THE INVENTION

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "%" and "percent" refers to percent by weight, unless otherwise is stated.

The term "particle size" relates to the ability of the particles to move through or be retained by sieve holes of a specific size. As used herein, the term "particle size" refers to the average particle size as determined according to European Pharmacopoeia 9.1 when using test method 2.9.38 particle size distribution estimation by analytical sieving, unless otherwise specifically is mentioned.

The term "particle" or similar wording is intended to denote a single, discrete composition of solid matter, such as a granule or individual elements in powder, having a certain size that may deviate considerable.

In the present context the term "release" refers to the released substance being liberated from the solid dosage form. In some embodiments, the process of releasing a substance corresponds to the substance being dissolved in saliva. The term "release" in the present context is intended to mean tested under "in vivo" conditions, if not stated otherwise. In the present context, when the solid dosage form is masticated, "in vivo" conditions is intended to mean that a sample is masticated with a chewing frequency of 60 chews pr. minute for a certain period of time in a test panel of 8 test persons, if not stated otherwise. These test persons abstain from eating and drinking at least 30 minutes before initiation of any test. The test persons are healthy persons appointed on an objective basis according to specified requirements.

The term "sustained release" or "extended release" is herein intended to mean prolonged release over time. The term "rapid release" or "quick release" or "high release" is herein intended to mean a higher content released for a given period of time.

By the phrase "texture" is meant a qualitative measure of the properties of the solid dosage form and of the overall mouth-feel experienced by the user during use. Thus, the term "texture" encompasses measurable quantities such as hardness as well as more subjective parameters related to the feel experienced by a user.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from a solid dosage form by the aid of active use of the solid dosage form in the oral cavity of the subject, whereby the active use is controlling the amount of substance released.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

Due to the poor solubility of certain active ingredients in physiological fluids, it is an unmet need to solubilize cannabinoids upon mixture with the body physiological fluids to facilitate bio-absorption. To overcome low oral bioavailability, various lipid-based drug delivery systems and self-emulsifying systems have been developed. Lipid-based delivery systems and particularly self-emulsifying drug delivery systems (SEDDS) have been demonstrated to increase the solubility, dissolution and bioavailability of many insoluble active ingredients. However, lipid-based and SEDDS delivery systems are very limited by the amount of active ingredient loading that has to be dissolved in the vehicle composition. Higher concentration of active ingredients are obtained using co-solvents, which enable loads of up to 30% in specific cases.

Particular challenges are considered to arise in formulating solid dosage forms with SEDDS. For instance, challenges may arise with obtaining a homogenous mixture where variations are avoided and a safe and convenient delivery may be obtained. Also, the general formulation of the solid dosage forms offering convenience to the user need not be compromised which is often the case if precaution is not taken, such as in cases where a high load of active ingredients is needed.

Particularly with respect to SEDDS, the formulation of the present invention may provide some clear benefits, both allowing a higher load of active ingredients and at the same time offer improved sensorics properties of the formulation during use. Other advantages are also present.

Importantly, the presence of SEDDS or at least a self-emulsifying agent was seen to act in synergy with increased saliva generation. While increased saliva generation was seen to distribute certain active ingredients and allocate a higher load of active ingredients to for instance mucosal surfaces, the presence of SEDDS or at least a self-emulsifying agent was seen to further increase the uptake of these active ingredients through oral surfaces. Accordingly, the synergy between the presence of SEDDS or at least a self-emulsifying agent and increased saliva generation according to the invention was a surprise to the inventors. In some embodiments, increased saliva generation may result in a higher exposure of the active ingredients to mucosal surfaces. The presence of SEDDS may work to increase the affinity of the active ingredients from this saliva to the mucosa. Particularly, the potential of SEDDS to have a high load of active ingredients further contributes to the synergy of the solid dosage form according to the invention in combination with improved saliva generation.

In the present context, SEDDS is a solid or liquid dosage form comprising an oil phase, a surfactant and optionally a co-surfactant, characterized primarily in that said dosage form can form oil-in-water emulsion spontaneously in the oral cavity or at ambient temperature (referring generally to body temperature, namely 37° C.). When a SEDDS enters the oral cavity, it is initially self-emulsified as emulsion droplets and rapidly dispersed throughout the oral cavity, and thus reducing the irritation caused by the direct contact of the active ingredient with the mucous membrane of the oral cavity, and hence helping on taste-masking active ingredients. In the oral cavity, the structure of the emulsion microparticulate will be changed or destroyed. The resulting microparticulate of micrometer or nanometer level can penetrate into the mucous membrane of for instance the oral cavity, and the absorbed oil droplets enter the blood circulation, thereby significantly improving the bioavailability of the active ingredient.

In an embodiment of the invention, the self-emulsifying system comprises one or more emulsifiers and one or more oil carriers.

In an embodiment of the invention, the self-emulsifying system comprises one or more emulsifiers, one or more oil carriers and one or more solubilizers.

In an embodiment of the invention, the self-emulsifying system comprises one or more emulsifiers, one or more oil carriers, one or more solubilizers and one or more solvents.

In an embodiment of the invention, the self-emulsifying system comprises one or more emulsifiers and one or more solvents.

In an embodiment of the invention, the self-emulsifying system comprises one or more emulsifiers that have both emulsifying and solubilizing properties.

In an embodiment of the invention, the self-emulsifying system comprises one or more emulsifiers that act as both an emulsifier and a carrier.

In an embodiment of the invention, the self-emulsifying system comprises one or more emulsifiers that act as both an emulsifier, a carrier and a solubilizer.

In an embodiment of the invention, the self-emulsifying system comprises one or more fatty acids, one or more glycerols, one or more waxes, one or more flavonoids and one or more terpenes.

In an embodiment of the invention, the self-emulsifying system comprises one or more emulsifiers that have an HLB-value of more than 6, preferably of 8-18.

In an embodiment of the invention, the one or more emulsifiers are selected from the group consisting of PEG-35 castor oil, PEG-6 oleoyl glycerides, PEG-6 linoleoyl glycerides, PEG-8 caprylic/capric glyceride, sorbitan monolaurate, sorbitan monooleate, polyoxyethylene (20) sorbitan monolaurate, polyoxyethylene (60) sorbitan monostearate, polyoxyethylene (80) sorbitan monooleate, lauroylpoloxyl-32 glycerides, stearoyl polyoxyl-32 glycerides, polyoxyl-32 stearate, propylene glycol mono laurate, propylene glycol di laurate, and mixtures and combinations thereof.

In an embodiment of the invention, the one or more emulsifiers comprise PEG-35 castor oil.

In an embodiment of the invention, the oil carrier is selected from the group consisting of natural fatty acids; medium-chain triglycerides of caprylic (C8) and capric (C10) acids; propylene glycol esters of caprylic (C8) and capric (C10) acids; mono-, di- and triglycerides of mainly linoleic (C18:2) and oleic (C18:1) acids; fatty acid 18:1 cis-9; natural fatty acids; mono-, di- and triglycerides of oleic (C18:1) acid, and mixtures and combinations thereof.

In an embodiment of the invention, the one or more solvents are selected from the group consisting of polyglyceryl-3 dioleate, 1,2-propandiol, polyethylene glycol 300, polyethylene glycol 400, diethylene glycol monoethyl ether, and mixtures and combinations thereof.

In an embodiment of the invention, the oil carrier is selected from the group consisting of corn oil, Labrafac lipophile WL1349, Labrafac PG, Maisine CC, oleic acid, olive oil, Peceol, and mixtures and combinations thereof.

In an embodiment of the invention, the one or more solvents are selected from the group consisting of polyglyceryl-3 dioleate, 1,2-propandiol, polyethylene glycol 300, polyethylene glycol 400, diethylene glycol monoethyl ether, and mixtures and combinations thereof.

In an embodiment of the invention, the one or more solubilizers are selected from the group consisting of lauroylpoloxyl-32 glycerides; stearoyl polyoxyl-32 glycerides; Polyoxyl-32 stearate; synthetic copolymer of ethylene oxide (80) and propylene oxide (27); polyvinyl caprolactam-polyvinyl acetate-polyethylene glycol graft co-polymer; alpha-, beta- or gamma cyclodextrins and derivatives thereof; pea proteins (globulins, albumins, glutelins proteins); and mixtures and combinations thereof.

In an embodiment of the invention, the formulation further comprises one or more lipids in addition to the lipid composition according to the invention.

The term "non-DC sugar alcohol particles" refers to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). In the present context, non-DC sugar alcohol particles include particles obtained by crystallization followed by milling which does not involve other sugar alcohols or binders. Thus, non-DC sugar alcohol particles are considered as particles consisting of non-DC sugar alcohol.

The term "DC sugar alcohol particles" refers to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC). Also, granulation of non-DC sugar alcohol with water as binder is considered to result in "DC sugar alcohol particles" in the present context.

The term "tableted" or "tablet" or "compressed" is intended to mean that the tablet composition is pressed in a tableting apparatus and mainly being composed of particulate matter. Although the terms imply a method step, in the present context, the terms are intended to mean the resulting tablet obtained in tableting a portion of particles. It is noted that a tablet or tableted composition that is mentioned to comprise particles eventually is to be understood as particles that have been pressed together in a tableting step.

The following description outlines explanations of how the tablet of the invention may be produced and further details of what may be added to the inventive composition.

Typically, the process of manufacture of the inventive tablet may be performed in a single tablet press, such as a rotary tablet press. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing of the tablets are performed at a force of 20 to 50 kN.

In one aspect of the invention, the "tablet" is intended to mean a "fast disintegrating tablet" ("FDT"), or similar wording, such as "orally disintegrating tablet" ("ODT"). If not stated otherwise, if the tablet according to the invention is made as one module, contrary to two or more modules, then the tablet is intended to be an FDT tablet. If on the other hand, the tablet is made of more than one module, such as two modules, such additional module is intended to be a "lozenge" module, which provides a longer disintegration time compared to the FDT module according to the invention. The combination of an "FDT" module and a "lozenge" module contributes to another aspect of the invention. A "lozenge" module according to the invention may also comprise elements from the "FDT" modules but is generally different in composition, providing an extended disintegration time.

The term "lozenge" is intended to cover that a "lozenge composition" has been "compressed" into a "lozenge module". In the present context, a "lozenge module" or similar wording is intended to mean that the module during use in the oral cavity is intended to be sucked or licked on. The term "lozenge" is given the ordinary meaning in the art of lozenges. The intention is that the lozenge module may not be chewed. The intention is also that the FDT module may not be chewed. Generally, the "lozenge module" of the present invention may disintegrate upon sucking or licked in minutes, contrary to seconds for orally disintegrating tablets (ODT) or fast disintegrating tablets (FDT) tablets. Hence, the intention is that the "lozenge module" is to deliver the one or more cannabinoids over a longer period of time than the FDT module, if the tablet is made as a combination of the two modules.

The term "module" is generally intended to be composed of a composition of matter with substantially the same characteristics throughout the module. Hence, if two module are present, then the two modules are different in composition and generally have two different characteristics throughout each module. In the present context, if only one module is present, then this module is considered an FDT tablet. On the other hand, if two modules are present, then the tablet is composed of an FDT tablet or FDT tablet module fused with a lozenge tablet or lozenge module. The term "fused" is intended to mean that the tablet is gathered together by means of compression force. Usually, if two modules are present, the lozenge module is made as the first module and the FDT module is made as the second module. The tablet may be composed of more than two modules. The lozenge module may in certain embodiments be replaced by a gum base module. In the present context, the invention provides an attractive bi-phasic delivery of masking, even if the delivery of nicotine is "single-phased".

The term "cannabinoid composition" is intended to mean a volume of matter comprising one or more cannabinoids. The cannabinoid composition may contain other components than cannabinoids. The cannabinoid composition may constitute cannabinoids. The cannabinoid composition may constitute one type of cannabinoids. The cannabinoid composition may constitute two types of cannabinoids. The cannabinoid composition may constitute two or more types of cannabinoids.

By the terms "water-insoluble gum base" or "gum base" or "gum base matrix" or similar wording is meant the mainly water-insoluble ingredients and hydrophobic gum base ingredients. The "gum base" may contain gum base polymers and plasticizers, waxes, emulsifiers, fats and/or fillers.

The term "natural resin", as used herein, means resinous compounds being either polyterpene derived from terpenes of natural origin or resinous compounds derived from gum rosin, wood rosin or tall-oil rosin.

Elastomers provide the rubbery, elastomeric and bouncing nature to the gum, which varies depending on this ingredient's chemical structure and how it may be compounded with other ingredients. Elastomers suitable for use in the gum base and gum of the present invention may include natural or synthetic types. Polyvinyl acetate elastomer plasticizers are not considered elastomers according to the invention.

Elastomers may be selected from the group consisting of styrene-butadiene copolymers, polyisobutylene, isobutylene-isoprene copolymers, polyethylene, polyurethane or any combination thereof. Preferred elastomers are styrene-butadiene copolymers (SBR), polyisobutylene and isobutylene-isoprene copolymers (BR).

Styrene-butadiene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene). The average molecular weight of SBR is <600,000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene). The average molecular weight of BR is in the range from 150,000 g/mole to 1,000,000 g/mole.

Polyisobutylene, or PIB as they may be called, type elastomers are polymers of 2-methylpropene. The low molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity to the gum. Average molecular weight may range from 120,000 to 1,000,000 g/mole.

Polybutene range in average molecular weight from about 5.000 g/mole to about 30.000 g/mole.

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang. Natural elastomers may also be applied in aspects of the present invention.

Elastomer plasticizers vary the firmness of the gum base. Their specificity on elastomer inter-molecular chain breaking (plasticizing) along with their varying softening points cause varying degrees of finished gum firmness and compatibility when used in base. Polyvinyl acetate elastomers plasticizers are examples of elastomer plasticizers of the present invention.

Natural resins may be selected from ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the solid dosage form comprises further ingredients selected from the group consisting of flavors, dry-binders, tableting aids, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

The solid dosage form according to the invention is manufactured by applying pressure to a content of particles by suitable compression means. The particles or powder is then pressed into a compact coherent tablet. The particles may for example comprise so-called primary particles or aggregated primary particles. When these are pressed, bonds are established between the particles or granules, thereby conferring a certain mechanical strength to the pressed tablet.

It should be noted that the above-introduced terms: powder, primary particles and aggregated primary particles may be somewhat misleading in the sense that the difference between primary particles and aggregated primary particles may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of aggregated primary particles. The definition adopted in the description of this invention is that aggregated primary particles refer to macro-particles comprising more or less preprocessed primary particles.

When pressure is applied to the particles, the bulk volume is reduced, and the amount of air is decreased. During this process energy is consumed. As the particles come into closer proximity to each other during the volume reduction process, bonds may be established between the particles or granules. The formation of bonds is associated with a reduction in the energy of the system as energy is released. Volume reduction takes place by various mechanisms and different types of bonds may be established between the particles or granules depending on the pressure applied and the properties of the particles or granules. The first thing that happens when a powder is pressed is that the particles are rearranged under low compaction pressures to form a closer packing structure. Particles with a regular shape appear to undergo rearrangement more easily than those of irregular shape. As the pressure increases, further rearrangement is prevented, and subsequent volume reduction is obtained by plastic and elastic deformation and/or fragmentation of the tablet particles. Brittle particles are likely to undergo fragmentation, i.e. breakage of the original particles into smaller units. Plastic deformation is an irreversible process resulting in a permanent change of particle shape, whereas the particles resume their original shape after elastic deformation. Evidently, both plastic and elastic deformation may occur, when compressing a solid dosage form.

Several studies of the bond types in pressed tablets have been made over the years, typically in the context of pharmaceuticals and several techniques of obtaining pressed tablets on the basis of available powders has been provided. Such studies have been quite focused on what happens when the volume reduction is performed and how the end-product may be optimized for the given purpose. Several refinements with respect to pressed tablets has for instance been made in the addition of for example binders in the tablet raw materials for the purpose of obtaining a sufficient strength to the final pressed tablet while maintaining acceptable properties, e.g. with respect to release.

Contrary to tableted chewing gum, conventional chewing gum may be manufactured by sequentially adding the various chewing gum ingredients to a commercially available mixer known in the art where the finished gum base is already present. After the initial ingredients have been thoroughly mixed, the gum mass is discharged from the mixer and shaped into the desired form such as by rolling into sheets and cutting into sticks, extruded into chunks or casting into pellets. Generally, the ingredients of conventional chewing gum may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added. The entire mixing procedure typically takes from thirty to forty minutes, but longer mixing times may sometimes be required. Those skilled in the art will recognize that many variations of the above-described procedure may be followed.

In some embodiments of the invention, the solid dosage form does not include conventional chewing gum, i.e., so-called extruded chewing gum.

In accordance with the invention, the tableted solid dosage form according to the invention may comprise about 0.1 to about 75% by weight of an outer coating applied onto the solid dosage form centre. Thus, suitable coating types include hard coatings, film coatings and soft coatings of any composition including those currently used in coating of tableted solid dosage form.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer, and it may moreover protect the solid dosage form centres for various reasons. In a typical process of providing the solid dosage form centres with a protective sugar coating, the solid dosage form centres are successively treated in suitable coating equipment with aqueous solutions of crystallizable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallizable sugar and/or polyol is applied onto the solid dosage form centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished solid dosage form element, such as about 10 to about 60% by weight, including about 15 to about 50% by weight.

In an embodiment of the invention, the product is a pouch.

In one aspect of the invention, the population of particles used for tableting may also be present in a pouch as a powder. Hence, this aspect of the invention includes the population of particles in a pouch without tableting, but as a powder or part of a powder with other powders or powder ingredients. It follows that the directly compressible (DC) and non-directly compressible (non-DC) sugar alcohol particles of the invention may be included in the pouch according to the invention. Additional embodiments pertaining to the population of particles of the invention will also be applicable when included in a pouch. It is noted that additional ingredients may be present in the pouch, such as water-soluble fibers or water-insoluble fibers, including microcrystalline cellulose.

According to an advantageous embodiment of the invention the pouch comprises a water-permeable membrane, such as a woven or non-woven fabric.

The pouches according to the invention comprise openings, where the characteristic opening dimension is adapted to a characteristic dimension of the population of particles so as to retain the matrix composition inside the pouch before use and/or to retain a part of the content inside the pouch during use.

In other words, according to the various embodiments, the pouch forms a membrane allowing passage of saliva and prevents or inhibits passage of at least a part of the content. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of the active ingredients from the pouch.

The powder is filled into pouches and is maintained in the pouch by a sealing. An ideal pouch is chemically and physically stable, it is pharmaceutically acceptable, it is insoluble in water, it is easy to fill with powder and seal, and it provides a semi-permeable membrane layer which prevent the powder from leaving the bag, but permit saliva and therein dissolved or sufficiently small suspended components from the powder in the pouch to pass through said pouch.

The pouch may be placed in the oral cavity by the user. Saliva then enters into the pouch, and the active ingredient and other components, which are soluble in saliva, start to dissolve and are transported with the saliva out of the pouch into the oral cavity. In some embodiments of the invention, the pouch may be masticated in a similar way as chewing a gum. This is particularly advantageous when the population of particles comprise gum base. Hence, the pouch may be masticated into a coherent residual containing water-insoluble components.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Antioxidants suitable for use include butylated hydroxy-anisole (BHA), butylated hydroxytoluene (BHT), betacarotenes, tocopherols, acidulants such as Vitamin C (ascorbic acid or corresponding salts (ascorbates)), propyl gallate, catechins, green tea extract other synthetic and natural types or mixtures thereof.

High intensity sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the high intensity sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another formulation component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

The invention, if desired, may include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which may have high affinity ligands of CB1 and CB2 receptors.

"Phytocannabinoids" are cannabinoids that originate in nature and can be found in the *cannabis* plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the *cannabis* plant. Examples include WIN 55212 and rimonabant.

An "isolated phytocannabinoid" or "isolated cannabinoid" is one which has been extracted from the *cannabis* plant and purified to such an extent that the additional components such as secondary and minor cannabinoids and the non-cannabinoid fraction have been substantially removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the *cannabis* plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from *cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *cannabis*, "botanical drug substances" derived from *cannabis* plants do not include highly purified, Pharmacopeial grade cannabinoids.

The term "*Cannabis* plant(s)" encompasses wild type *Cannabis sativa* and also variants thereof, including *cannabis* chemovars which naturally contain different amounts of the individual cannabinoids, *Cannabis sativa* subspecies *indica* including the variants var. *indica* and var. *kafiris-*

*tanica, Cannabis indica, Cannabis ruderalis* and also plants which are the result of genetic crosses, self-crosses or hybrids thereof. The term "*Cannabis* plant material" is to be interpreted accordingly as encompassing plant material derived from one or more *cannabis* plants. For the avoidance of doubt it is hereby stated that "*cannabis* plant material" includes dried *cannabis* biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the *cannabis* plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body. Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids. Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia.

In one embodiment the cannabinoid is palmitoylethanolamide (PEA) which is an endogenous fatty acid amide belonging to the class of nuclear factor agonists.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the solid dosage form of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia. In a further aspect of the present invention, the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumors, neuropathic pain, *cannabis* use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

EXAMPLES

Example 1

Premix: Hydrogenated Vegetable Oil (HVO) Added to a Mixture of Isolated CBD and Sweetener Mannitol (Pearlitol 150SD) provided from Roquette in an amount of about 1780 g was added to a Lödige high shear mixer and heated to a temperature of about 55 Degree Celsius. Thereafter, a cannabinoid powder composition comprising CBD isolate from *cannabis* plant tissues (phytocannabinoid) with a 99% content of CBD provided by Medical Hemp (batch number MH B18592) in an amount of about 140 g was sieved through a 600 microns sieve and added to the sweetener powder composition. This mixture was mixed in the mixer at a speed of about 80 rpm for about 5 minutes. After activation of the chopper (about 600 rpm)

of the Lödige mixer, HVO provided from AAK under the tradename Akocrem NT 76-33 with a melting temperature of 30-35 Degree Celsius was melted at a temperature of about 55 Degree Celsius and added to the mixture in an amount of about 80 g. After adding the lipid composition, the temperature in the mixer was about 49 Degree Celsius, and the mixture was further mixed for about 10 minutes. After 10 minutes, the temperature of the final mixture was about 51 Degree Celsius. A total of 2 kg mixture powder premix was made in which the CBD content was about 70 mg/g.

TABLE 1

Hydrogenated Vegetable Oil (HVO) having been preheated to a temperature of about 55 Degree Celsius. Variation in the content of CBD isolate (purity 99%). Sample 102 corresponds to the procedure above, the other samples are adjusted to the variation in contents.

| | Powder Premix Number | | | | |
| | 100 | 101 | 102 | 103 | 104 |
| Raw material name | Content [%] | Content [%] | Content [%] | Content [%] | Content [%] |
| --- | --- | --- | --- | --- | --- |
| Mannitol | 94.0 | 91.0 | 89.0 | 87.0 | 84.0 |
| CBD isolate (purity 99%) | 2.0 | 5.0 | 7.0 | 9.0 | 12.0 |
| HVO | 4.0 | 4.0 | 4.0 | 4.0 | 4.0 |
| Total | 100 | 100 | 100 | 100 | 100 |

TABLE 2

Hydrogenated Vegetable Oil (HVO) having been preheated to a temperature of about 55 Degree Celsius. Variation in the content of HVO. Sample 112 corresponds to the procedure above, the other samples are adjusted to the variation in contents.

| | Powder Premix Number | | | | |
| | 110 | 111 | 112 | 113 | 114 |
| Raw material name | Content [%] | Content [%] | Content [%] | Content [%] | Content [%] |
| --- | --- | --- | --- | --- | --- |
| Mannitol | 93.0 | 90.5 | 89.0 | 87.0 | 83.0 |
| CBD isolate (purity 99%) | 7.0 | 7.0 | 7.0 | 7.0 | 7.0 |
| HVO | 1.0 | 2.5 | 4.0 | 6.0 | 10.0 |
| Total | 100 | 100 | 100 | 100 | 100 |

TABLE 3

Hydrogenated Vegetable Oil (HVO) having been preheated to a temperature of about 55 Degree Celsius. Variation in the type of sweetener. Here mannitol was replaced by other sweeteners. Sample 122 corresponds to the procedure above.

| | Powder Premix Number | | | | |
| | 120 | 121 | 122 | 123 | 124 |
| Raw material name | Content [%] | Content [%] | Content [%] | Content [%] | Content [%] |
| --- | --- | --- | --- | --- | --- |
| Mannitol | | | 89.0 | | |
| Isomalt | 89.0 | | | | |
| Maltitol | | | | 89.0 | |
| Xylitol | | 89.0 | | | |
| Dextrose | | | | | 89.0 |
| CBD isolate (purity 99%) | 7.0 | 7.0 | 7.0 | 7.0 | 7.0 |
| HVO | 4.0 | 4.0 | 4.0 | 4.0 | 4.0 |
| Total | 100 | 100 | 100 | 100 | 100 |

Example 2

Premix: Miglyol Added to a Mixture of Isolated CBD and Sweetener

Mannitol (Pearlitol 150SD) provided from Roquette in an amount of about 1780 g was added to a Lödige high shear mixer and heated to a temperature of about 55 Degree Celsius. Thereafter, a cannabinoid powder composition comprising CBD isolate from *cannabis* plant tissues (phytocannabinoid) with a 99% content of CBD provided by Medical Hemp (batch number MH B18592) in an amount of about 140 g was sieved through a 600 microns sieve and added to the sweetener powder composition. This mixture was mixed in the mixer at a speed of about 80 rpm for about 5 minutes. After activation of the chopper (about 600 rpm) of the Lödige mixer, Medium Chain Triglyceride (MCT), Miglyol 812, provided from Sasol was added to the mixture during a period of about 3 minutes in an amount of about 80 g. After adding the Miglyol 812, the mixture was further mixed for about 10 minutes. After 10 minutes, the temperature of the final mixture was about 51 Degree Celsius. A total of 2 kg mixture powder premix was made in which the CBD content was about 70 mg/g.

TABLE 4

Miglyol 812 having not been preheated. Variation in the content of CBD isolate (purity 99%). Sample 202 corresponds to the procedure above, the other samples are adjusted to the variation in contents.

| | Powder Premix Number | | | | |
| | 200 | 201 | 202 | 203 | 204 |
| Raw material name | Content [%] | Content [%] | Content [%] | Content [%] | Content [%] |
| --- | --- | --- | --- | --- | --- |
| Mannitol | 94.0 | 91.0 | 89.0 | 87.0 | 84.0 |
| CBD isolate (purity 99%) | 2.0 | 5.0 | 7.0 | 9.0 | 12.0 |
| Miglyol 812 | 4.0 | 4.0 | 4.0 | 4.0 | 4.0 |
| Total | 100 | 100 | 100 | 100 | 100 |

TABLE 5

Miglyol 812 having not been preheated. Variation in the content of Miglyol 812. Sample 212 corresponds to the procedure above, the other samples are adjusted to the variation in contents.

| | Powder Premix Number | | | | |
| | 210 | 211 | 212 | 213 | 214 |
| Raw material name | Content [%] | Content [%] | Content [%] | Content [%] | Content [%] |
| --- | --- | --- | --- | --- | --- |
| Mannitol | 93.0 | 90.5 | 89.0 | 87.0 | 83.0 |
| CBD isolate (purity 99%) | 7.0 | 7.0 | 7.0 | 7.0 | 7.0 |
| Miglyol 812 | 1.0 | 2.5 | 4.0 | 6.0 | 10.0 |
| Total | 100 | 100 | 100 | 100 | 100 |

TABLE 6

Miglyol having not been preheated unless specifically denoted.
Variation in the type of Miglyol. Sample 222 corresponds
to the procedure above. Miglyol 829 in Powder Premix Number
223 is heated to about 50° C. in order to work. Powder
Premix Number 224 is a comparative powder.

| Raw material name | Powder Premix Number | | | | |
|---|---|---|---|---|---|
| | 220 Content [%] | 221 Content [%] | 222 Content [%] | 223 Content [%] | 224 Content [%] |
| Mannitol | 89.0 | 89.0 | 89.0 | 89.0 | 89.0 |
| CBD isolate (purity 99%) | 7.0 | 7.0 | 7.0 | 7.0 | 7.0 |
| Miglyol 812 | | | 4.0 | | |
| Miglyol 810 | 4.0 | | | | |
| Miglyol 818 | | 4.0 | | | |
| Miglyol 829 | | | | 4.0 | |
| Miglyol 840 | | | | | 4.0 |
| Total | 100 | 100 | 100 | 100 | 100 |

TABLE 7

Miglyol 812 having not been preheated. Variation in the
type of sweetener. Here mannitol was replaced by other
sweeteners. Sample 232 corresponds to the procedure above.

| Raw material name | Powder Premix Number | | | | |
|---|---|---|---|---|---|
| | 230 Content [%] | 231 Content [%] | 232 Content [%] | 233 Content [%] | 234 Content [%] |
| Mannitol | | | 89.0 | | |
| Isomalt | 89.0 | | | | |
| Maltitol | | | | 89.0 | |
| Xylitol | | 89.0 | | | |
| Dextrose | | | | | 89.0 |
| CBD isolate (purity 99%) | 7.0 | 7.0 | 7.0 | 7.0 | 7.0 |
| Miglyol 812 | 4.0 | 4.0 | 4.0 | 4.0 | 4.0 |
| Total | 100 | 100 | 100 | 100 | 100 |

Example 3

Premix: High Load-Hydrogenated Vegetable Oil (HVO) Added to a Mixture of Isolated CBD and Sweetener Mannitol (Pearlitol 150SD) provided from Roquette in an amount of about 1220 g was added to a Lödige high shear mixer and heated to a temperature of about 55 Degree Celsius. Thereafter, a cannabinoid powder composition comprising CBD isolate from *cannabis* plant tissues (phytocannabinoid) with a 99% content of CBD provided by Medical Hemp (batch number MH B18592) in an amount of about 700 g was sieved through a 600 microns sieve and added to the sweetener powder composition. This mixture was mixed in the mixer at a speed of about 80 rpm for about 5 minutes. After activation of the chopper (about 600 rpm) of the Lödige mixer, HVO provided from AAK under the tradename Akocrem NT 76-33 with a melting temperature of 30-35 Degree Celsius was melted at a temperature of about 55 Degree Celsius and added to the mixture in an amount of about 80 g. After adding the lipid composition, the temperature in the mixer was about 49 Degree Celsius, and the mixture was further mixed for about 10 minutes. After 10 minutes, the temperature of the final mixture was about 51 Degree Celsius. A total of 2 kg mixture powder premix was made in which the CBD content was about 350 mg/g.

TABLE 8

Hydrogenated Vegetable Oil (HVO) having been preheated
to a temperature of about 55 Degree Celsius. Variation
in the content of CBD isolate (purity 99%). Sample
302 corresponds to the procedure above, the other
samples are adjusted to the variation in contents.

| Raw material name | Powder Premix Number | | | | |
|---|---|---|---|---|---|
| | 300 Content [%] | 301 Content [%] | 302 Content [%] | 303 Content [%] | 304 Content [%] |
| Mannitol | 71.0 | 66.0 | 61.0 | 56.0 | 51.0 |
| CBD isolate (purity 99%) | 25.0 | 30.0 | 35.0 | 40.0 | 45.0 |
| HVO | 4.0 | 4.0 | 4.0 | 4.0 | 4.0 |
| Total | 100 | 100 | 100 | 100 | 100 |

TABLE 9

Hydrogenated Vegetable Oil (HVO) having been
preheated to a temperature of about 55 Degree Celsius.
Variation in the content of HVO.

| Raw material name | Powder Premix Number | | | | |
|---|---|---|---|---|---|
| | 310 Content [%] | 311 Content [%] | 312 Content [%] | 313 Content [%] | 314 Content [%] |
| Mannitol | 64.0 | 62.5 | 61.0 | 59.0 | 55.0 |
| CBD isolate (purity 99%) | 35.0 | 35.0 | 35.0 | 35.0 | 35.0 |
| HVO | 1.0 | 2.5 | 4.0 | 6.0 | 10.0 |
| Total | 100 | 100 | 100 | 100 | 100 |

Sample 312 corresponds to the procedure above, the other samples are adjusted to the variation in contents.

TABLE 10

Hydrogenated Vegetable Oil (HVO) having been
preheated to a temperature of about 55 Degree Celsius.
Variation in the type of sweetener. Here mannitol
was replaced by other sweeteners.

| Raw material name | Powder Premix Number | | | | |
|---|---|---|---|---|---|
| | 320 Content [%] | 321 Content [%] | 322 Content [%] | 323 Content [%] | 324 Content [%] |
| Mannitol | | | 61.0 | | |
| Isomalt | 61.0 | | | | |
| Maltitol | | | | 61.0 | |
| Xylitol | | 61.0 | | | |
| Dextrose | | | | | 61.0 |
| CBD isolate (purity 99%) | 35.0 | 35.0 | 35.0 | 35.0 | 35.0 |
| HVO | 4.0 | 4.0 | 4.0 | 4.0 | 4.0 |
| Total | 100 | 100 | 100 | 100 | 100 |

Sample 322 corresponds to the procedure above.

Example 4

Premix: Hydrogenated Vegetable Oil (HVO) Mixture with Isolated CBD Added to Sweetener Mannitol (Pearlitol 150SD) provided from Roquette in an amount of about 721 g was added to a Lödige high shear mixer and heated to a temperature of about 55 Degree Celsius. Thereafter, a cannabinoid powder composition comprising CBD isolate from *cannabis* plant tissues (phytocannabinoid) with a 99% content of CBD provided by Medical Hemp (batch number MH B18592) in an amount of about 91 g was mixed with HVO provided from AAK under the tradename Akocrem NT 76-33 with a melting temperature of 30-35 Degree Celsius in an amount of about 29 g. While stirring, the CBD-HVO mixture was heated to a temperature of about 60 Degree Celsius to form a liquid solution of CBD in HVO. The mixture of CBD and HVO corresponding to a ratio of about 75/25 (hereafter denoted 75% CBD mixture) was then added to the sweetener powder composition in an amount of about 79 g. After adding the lipid composition, the mixture was mixed for about 10 minutes. A total of 800 g mixture powder premix was made.

TABLE 11

Hydrogenated Vegetable Oil (HVO) having been heated to a temperature of about 60 Degree Celsius after mixing with 99% purity CBD (75% CBD mixture). Variation in the content of CBD (75% CBD mixture).

| | Powder Premix Number | | | | |
| | 400 | 401 | 402 | 403 | 404 |
| Raw material name | Content [%] | Content [%] | Content [%] | Content [%] | Content [%] |
|---|---|---|---|---|---|
| Mannitol | 94.1 | 92.0 | 90.1 | 88.1 | 85.1 |
| CBD isolate (75% CBD mixture) | 5.9 | 7.9 | 9.9 | 11.9 | 14.9 |
| Total | 100 | 100 | 100 | 100 | 100 |

Sample 402 corresponds to the procedure above, the other samples are adjusted to the variation in contents.

TABLE 12

Hydrogenated Vegetable Oil (HVO) having been heated to a temperature of about 60 Degree Celsius after mixing with 99% purity CBD (X % CBD mixture). Variation in the content of CBD in mixture with HVO.

| | Powder Premix Number | | | | |
| | 410 | 411 | 412 | 413 | 414 |
| Raw material name | Content [%] | Content [%] | Content [%] | Content [%] | Content [%] |
|---|---|---|---|---|---|
| Mannitol | 90.1 | 90.1 | 90.1 | 90.1 | 90.1 |
| CBD isolate (X % CBD mixture) | 9.9 (50%)* | 9.9 (60%)* | 9.9 (75%)* | 9.9 (80%)* | 9.9 (90%)* |
| Total | 100 | 100 | 100 | 100 | 100 |

*denotes the percentage X of CBD in "X % CBD mixture".
Sample 412 corresponds to the procedure above, the other samples are adjusted to the variation in contents.

TABLE 13

Hydrogenated Vegetable Oil (HVO) having been heated to a temperature of about 60 Degree Celsius after mixing with 99% CBD (75% CBD mixture). Variation in the type of sweetener. Here mannitol was replaced by other sweeteners.

| | Powder Premix Number | | | | |
| | 420 | 421 | 422 | 423 | 424 |
| Raw material name | Content [%] | Content [%] | Content [%] | Content [%] | Content [%] |
|---|---|---|---|---|---|
| Mannitol | | | 90.1 | | |
| Isomalt | 90.1 | | | | |
| Maltitol | | | | 90.1 | |
| Xylitol | | 90.1 | | | |

TABLE 13-continued

Hydrogenated Vegetable Oil (HVO) having been heated to a temperature of about 60 Degree Celsius after mixing with 99% CBD (75% CBD mixture). Variation in the type of sweetener. Here mannitol was replaced by other sweeteners.

| | Powder Premix Number | | | | |
| | 420 | 421 | 422 | 423 | 424 |
| Raw material name | Content [%] | Content [%] | Content [%] | Content [%] | Content [%] |
|---|---|---|---|---|---|
| Dextrose | | | | | 90.1 |
| CBD isolate (75% CBD mixture) | 9.9 | 9.9 | 9.9 | 9.9 | 9.9 |
| Total | 100 | 100 | 100 | 100 | 100 |

Sample 422 corresponds to the procedure above.

Example 5

Premix: Miglyol Mixture with Isolated CBD Added to Sweetener

Mannitol (Pearlitol 150SD) provided from Roquette in an amount of about 721 g was added to a Lödige high shear mixer and heated to a temperature of about 55 Degree Celsius. Thereafter, a cannabinoid powder composition comprising CBD isolate from *cannabis* plant tissues (phytocannabinoid) with a 99% content of CBD provided by Medical Hemp (batch number MH B18592) in an amount of about 91 g was mixed with Medium Chain Triglyceride (MCT), Miglyol 812, provided from Sasol in an amount of about 29 g. While stirring, the CBD-MCT mixture was heated to a temperature of about 70 Degree Celsius to form a liquid solution of CBD in MCT. The mixture of CBD and Miglyol 812 corresponding to a ratio of about 75/25 (hereafter denoted 75% CBD mixture) was then added to the sweetener powder composition in an amount of about 79 g. After adding the lipid composition, the mixture was mixed for about 10 minutes. A total of 800 g mixture powder premix was made.

TABLE 14

Miglyol 812 mixed with 99% purity CBD followed by heating (75% CBD mixture). Variation in the content of CBD (75% CBD mixture).

| | Powder Premix Number | | | | |
| | 500 | 501 | 502 | 503 | 504 |
| Raw material name | Content [%] | Content [%] | Content [%] | Content [%] | Content [%] |
|---|---|---|---|---|---|
| Mannitol | 94.1 | 92.0 | 90.1 | 88.1 | 85.1 |
| CBD isolate (75% CBD mixture) | 5.9 | 7.9 | 9.9 | 11.9 | 14.9 |
| Total | 100 | 100 | 100 | 100 | 100 |

Sample 502 corresponds to the procedure above, the other samples are adjusted to the variation in contents.

TABLE 15

Miglyol 812 mixed with 99% CBD followed by heating (X % CBD mixture). Variation in the content of CBD in mixture with Miglyol 812.

| | Powder Premix Number | | | | |
|---|---|---|---|---|---|
| Raw material name | 510 Content [%] | 511 Content [%] | 512 Content [%] | 513 Content [%] | 514 Content [%] |
| Mannitol | 90.1 | 90.1 | 90.1 | 90.1 | 90.1 |
| CBD isolate (X % CBD mixture) | 9.9 (50%)* | 9.9 (60%)* | 9.9 (75%)* | 9.9 (80%)* | 9.9 (90%)* |
| Total | 100 | 100 | 100 | 100 | 100 |

*denotes the percentage X of CBD in "X % CBD mixture".
Sample 512 corresponds to the procedure above, the other samples are adjusted to the variation in contents.

TABLE 16

Miglyol 812 mixed with 99% CBD followed by heating (75% CBD mixture). Variation in the type of sweetener. Here mannitol was replaced by other sweeteners.

| | Powder Premix Number | | | | |
|---|---|---|---|---|---|
| Raw material name | 520 Content [%] | 521 Content [%] | 522 Content [%] | 523 Content [%] | 524 Content [%] |
| Mannitol | | | 90.1 | | |
| Isomalt | 90.1 | | | | |
| Maltitol | | | | 90.1 | |
| Xylitol | | 90.1 | | | |
| Dextrose | | | | | 90.1 |
| CBD isolate (75% CBD mixture) | 9.9 | 9.9 | 9.9 | 9.9 | 9.9 |
| Total | 100 | 100 | 100 | 100 | 100 |

Sample 522 corresponds to the procedure above.

Example 6

Premix: Comparative Samples—without Triglyceride Lipids

Mannitol (Pearlitol 150SD) provided from Roquette was added to a Lödige high shear mixer and heated to a temperature of about 55 Degree Celsius. Thereafter, a cannabinoid powder composition comprising CBD isolate from *cannabis* plant tissues (phytocannabinoid) with a purity about 99% of CBD provided by either Medical Hemp (batch number MH18592) or Valens (batch number BVA032013) was sieved through a 600 microns sieve and added to the sweetener powder composition. This mixture was mixed at a speed of about 80 rpm for about 10 minutes. No lipid composition was present.

TABLE 17

Variation in the content of CBD isolate.

| | Powder Premix Number | | | | |
|---|---|---|---|---|---|
| Raw material name | 600 Content [%] | 601 Content [%] | 602 Content [%] | 603 Content [%] | 604 Content [%] |
| Mannitol | 90.0 | 85.0 | 80.0 | 75.0 | 70.0 |
| CBD isolate (MH18592) | 10.0 | 15.0 | 20.0 | 25.0 | 30.0 |
| Total | 100 | 100 | 100 | 100 | 100 |

TABLE 18

Variation in the content of CBD isolate.

| | Powder Premix Number | | | | |
|---|---|---|---|---|---|
| Raw material name | 610 Content [%] | 611 Content [%] | 612 Content [%] | 613 Content [%] | 614 Content [%] |
| Mannitol | 92.0 | 94.0 | 96.0 | 97.0 | 98.0 |
| CBD isolate (MH18592) | 8.0 | 6.0 | 4.0 | 3.0 | 2.0 |
| Total | 100 | 100 | 100 | 100 | 100 |

TABLE 19

Variation in the content of CBD isolate. Difference in CBD isolate source.

| | Powder Premix Number | | | | |
|---|---|---|---|---|---|
| Raw material name | 620 Content [%] | 621 Content [%] | 622 Content [%] | 623 Content [%] | 624 Content [%] |
| Mannitol | 90.0 | 85.0 | 80.0 | 75.0 | 70.0 |
| CBD isolate (BVA032013) | 10.0 | 15.0 | 20.0 | 25.0 | 30.0 |
| Total | 100 | 100 | 100 | 100 | 100 |

Example 7

Preparation of Tablet with Two Layers

Tablets were made based on the CBD containing powder mixtures of Examples 1-2 with each layer having a weight of about 50% of the total tablet. The total weight of the tablets were 1800 mg. The tablets were made with a standard tablet pressing machine (3090i, available from Fette GmbH) comprising dosing apparatus (P 3200 C, available from Fette GmbH, Germany). Punch used: 16.00 mm round punches. Rotor speed used was 11 rpm.

A first layer (denoted layer 1) comprising the CBD containing powder mixture made in Examples 1-2 and additional ingredients was prepared and tableted before tableting the layer comprising gum base (denoted layer 2). Layer 1 with a weight of about 900 mg was compressed at a compression force of about 5 kN. Hereafter, layer 2 with a weight of about 900 mg and comprising gum base and additional ingredients was pressed on top of layer 1 at a compression force of 40 kN. The tablet machine was commissioned by adjusting the fill depth and compression force so the weight and hardness of tablets match the acceptance criteria. A pre-compression force could be included to avoid capping.

TABLE 20

In all of the tablet examples, the amount of the various ingredients is given as % by weight of the tablet.

| Raw material name | Content [%] Layer 1-900 mg | Content [%] Layer 2-900 mg |
|---|---|---|
| Powder Premix Sample from Example 1 | 16.1 | |
| Flavors | 1.2 | 1.8 |
| High-intensity sweeteners | 0.1 | 0.3 |

TABLE 20-continued

In all of the tablet examples, the amount of the various
ingredients is given as % by weight of the tablet.

| Raw material name | Content [%] Layer 1-900 mg | Content [%] Layer 2-900 mg |
|---|---|---|
| Lubricant | 3.0 | 3.0 |
| Mannitol | 29.6 | |
| Xylitol DC | | 12.7 |
| Gum base | | 31.5 |
| Other components | | 0.7 |
| Total | 50 | 50 |

TABLE 21

In all of the tablet examples, the amount of the various
ingredients is given as % by weight of the tablet.

| Raw material name | Content [%] Layer 1-900 mg | Content [%] Layer 2-900 mg |
|---|---|---|
| Powder Premix Sample from Example 2 | 16.1 | |
| Flavors | 1.2 | 1.8 |
| High-intensity sweeteners | 0.1 | 0.3 |
| Lubricant | 3.0 | 3.0 |
| Mannitol | 29.6 | |
| Xylitol DC | | 12.7 |
| Gum base | | 31.5 |
| Other components | | 0.7 |
| Total | 50 | 50 |

TABLE 22

In all of the tablet examples, the amount of the various
ingredients is given as % by weight of the tablet.

| Raw material name | Content [%] Layer 1-900 mg | Content [%] Layer 2-900 mg |
|---|---|---|
| Powder Premix Sample from Example 2 | 16.1 | |
| Flavors | 1.2 | 1.8 |
| High-intensity sweeteners | 0.1 | 0.3 |
| Silicon dioxide * | 0.3 | |
| Lubricant | 3.0 | 3.0 |
| Mannitol | 29.3 | |
| Xylitol DC | | 12.7 |
| Gum base | | 31.5 |
| Other components | | 0.7 |
| Total | 50 | 50 |

* Silicon dioxide may optionally be added at the stage of preparing the mixture in Example 2

Example 8

Preparation of Tablet with Two Layers

Tablets were made based on the CBD containing powder mixtures of Example 3 with each layer having a weight of about 50% of the total tablet. The total weight of the tablets were 1800 mg. The tablets were made with a standard tablet pressing machine (3090i, available from Fette GmbH) comprising dosing apparatus (P 3200 C, available from Fette GmbH, Germany). Punch used: 16.00 mm round punches. Rotor speed used was 11 rpm.

A first layer (denoted layer 1) comprising the CBD containing powder mixture made in Example 3 and additional ingredients was prepared and tableted before tableting the layer comprising gum base (denoted layer 2). Layer 1 was compressed at a compression force of about 5 kN. Hereafter, layer 2 comprising gum base and additional ingredients was pressed on top of layer 1 at a compression force of 40 kN. The tablet machine was commissioned by adjusting the fill depth and compression force so the weight and hardness of tablets match the acceptance criteria. A pre-compression force could be included to avoid capping.

TABLE 23

In all of the tablet examples, the amount of the various
ingredients is given as % by weight of the tablet.

| Raw material name | Content [%] Layer 1-900 mg | Content [%] Layer 2-900 mg |
|---|---|---|
| Powder Premix Sample from Example 3 | 7.9 | |
| Flavors | 1.2 | 1.8 |
| High-intensity sweeteners | 0.1 | 0.3 |
| Silicon dioxide * | 0.3 | |
| Lubricant | 3.0 | 3.0 |
| Mannitol | 37.5 | |
| Xylitol DC | | 12.7 |
| Gum base | | 31.5 |
| Other components | | 0.7 |
| Total | 50 | 50 |

* Silicon dioxide may optionally be added at the stage of preparing the mixture in Example 3

TABLE 24

In all of the tablet examples, the amount of the various
ingredients is given as % by weight of the tablet.

| Raw material name | Content [%] Layer 1-900 mg | Content [%] Layer 2-900 mg |
|---|---|---|
| Powder Premix Sample from Example 3 | 15.8 | |
| Flavors | 1.2 | 1.8 |
| High-intensity sweeteners | 0.1 | 0.3 |
| Silicon dioxide * | 0.3 | |
| Lubricant | 3.0 | 3.0 |
| Mannitol | 29.6 | |
| Xylitol DC | | 12.7 |
| Gum base | | 31.5 |
| Other components | | 0.7 |
| Total | 50 | 50 |

* Silicon dioxide may optionally be added at the stage of preparing the mixture in Example 3

Example 9

Preparation of Tablet with Two Layers

Tablets were made based on the CBD containing powder mixtures of Examples 4-5 with two layers where one layer having a weight of about 45% of the total tablet and another layer having a weight of about 55% (the layer without CBD). The total weight of the tablets were 1800 mg. The tablets were made with a standard tablet pressing machine (3090i, available from Fette GmbH) comprising dosing apparatus (P 3200 C, available from Fette GmbH, Germany). Punch used: 16.00 mm round punches. Rotor speed used was 11 rpm.

A first layer (denoted layer 1) comprising the CBD containing powder mixture made in Examples 1-2 and additional ingredients was prepared and tableted before tableting the layer comprising gum base (denoted layer 2). Layer 1 was compressed at a compression force of about 5 kN. Hereafter, layer 2 comprising gum base and additional ingredients was pressed on top of layer 1 at a compression force of 40 kN. The tablet machine was commissioned by adjusting the fill depth and compression force so the weight and hardness of tablets match the acceptance criteria. A pre-compression force could be included to avoid capping.

TABLE 25

In all of the tablet examples, the amount of the various ingredients is given as % by weight of the tablet.

| Raw material name | Content [%] Layer 1-810 mg | Content [%] Layer 2-990 mg |
|---|---|---|
| Powder Premix Sample from Example 4 | 15.0 | |
| Flavors | 1.0 | 2.4 |
| High-intensity sweeteners | 0.1 | 0.1 |
| Lubricant | 2.5 | 3.2 |
| Mannitol | 26.4 | |
| Xylitol DC | | 15.6 |
| Gum base | | 33 |
| Other components | | 0.7 |
| Total | 45 | 55 |

TABLE 26

In all of the tablet examples, the amount of the various ingredients is given as % by weight of the tablet.

| Raw material name | Content [%] Layer 1-810 mg | Content [%] Layer 2-990 mg |
|---|---|---|
| Powder Premix Sample from Example 5 | 15.0 | |
| Flavors | 1.0 | 2.4 |
| High-intensity sweeteners | 0.1 | 0.1 |
| Lubricant | 2.5 | 3.2 |
| Mannitol | 26.4 | |
| Xylitol DC | | 15.6 |
| Gum base | | 33 |
| Other components | | 0.7 |
| Total | 45 | 55 |

Example 10

Comparative Tablets with Two Layers

Tablets were made based on the CBD containing powder mixtures of Example 6 with two layers where one layer having a weight of about 45% of the total tablet and another layer having a weight of about 55% (the layer without CBD). The total weight of the tablets were 1800 mg. The tablets were made with a standard tablet pressing machine (3090i, available from Fette GmbH) comprising dosing apparatus (P 3200 C, available from Fette GmbH, Germany). Punch used: 16.00 mm round punches. Rotor speed used was 11 rpm.

A first layer (denoted layer 1) comprising the CBD containing powder mixture made in Examples 1-2 and additional ingredients was prepared and tableted before tableting the layer comprising gum base (denoted layer 2). Layer 1 was compressed at a compression force of about 5 kN. Hereafter, layer 2 comprising gum base and additional ingredients was pressed on top of layer 1 at a compression force of 40 kN. The tablet machine was commissioned by adjusting the fill depth and compression force so the weight and hardness of tablets match the acceptance criteria. A pre-compression force could be included to avoid capping.

TABLE 27

In all of the tablet examples, the amount of the various ingredients is given as % by weight of the tablet.

| Raw material name | Content [%] Layer 1-810 mg | Content [%] Layer 2-990 mg |
|---|---|---|
| Powder Premix Sample from Example 6 | 5.6 | |
| Flavors | 1.0 | 2.4 |
| High-intensity sweeteners | 0.1 | 0.1 |
| Lubricant | 2.5 | 3.2 |
| Mannitol | 35.8 | 6.4 |
| Xylitol DC | | 9.2 |
| Gum base | | 33 |
| Other components | | 0.7 |
| Total | 45 | 55 |

TABLE 28

In all of the tablet examples, the amount of the various ingredients is given as % by weight of the tablet.

| Raw material name | Content [%] Layer 1-810 mg | Content [%] Layer 2-990 mg |
|---|---|---|
| Powder Premix Sample from Example 6 | 14.1 | |
| Flavors | 1.0 | 2.4 |
| High-intensity sweeteners | 0.1 | 0.1 |
| Lubricant | 2.5 | 3.2 |
| Mannitol | 27.3 | 6.4 |
| Xylitol DC | | 9.2 |
| Gum base | | 33 |
| Other components | | 0.7 |
| Total | 45 | 55 |

TABLE 29

In all of the tablet examples, the amount of the various ingredients is given as % by weight of the tablet.

| Raw material name | Content [%] Layer 1-810 mg | Content [%] Layer 2-990 mg |
|---|---|---|
| Powder Premix Sample from Example 6 | 2.8 | |
| Flavors | 1.0 | 2.4 |
| High-intensity sweeteners | 0.1 | 0.1 |
| Lubricant | 2.5 | 3.2 |
| Mannitol | 38.6 | 6.4 |
| Xylitol DC | | 9.2 |
| Gum base | | 33 |
| Other components | | 0.7 |
| Total | 45 | 55 |

Example 11A

Test Method for Content Uniformity in Powder Premixtures and Powder Blends

Content Uniformity (CU), ie. homogeneity of the CBD active substance in powder premixtures (Powder Premix Samples) as well as powder blends which are mixtures with additional ingredients to be processed into the oral dosage form (Powder Blends), is determined according to European Pharmacopoeia 10.8 using test method 2.9.40 Uniformity of dosage units.

At least 5 samples each having the same fixed weight in the range of 0.25-2 gram are taken from the powder mixture to be analyzed. For each sample, the content of CBD active is analyzed by means of standard HPLC techniques. Content Uniformity is then calculated as the relative standard deviation (RSD) of the individual results.

Example 11B

Test Method for Content Uniformity in Solid Dosage Forms

Content Uniformity (CU), ie. homogeneity of the CBD active substance in solid dosage forms, is determined according to European Pharmacopoeia 10.8 using test method 2.9.40 Uniformity of dosage units.

At least 10 samples are taken from the solid dosage form, eg. tablets, to be analyzed. For each sample, the content of CBD active is analyzed by means of standard HPLC techniques. Content Uniformity is then calculated as the relative standard deviation (RSD) of the individual results.

Example 12

In Vivo Testing of Release in Solid Dosage Forms

A sample solid dosage form was tested in a test panel of 8 test persons. Test subjects abstain from eating and drinking at least 30 minutes before initiation of any test. The test person was a healthy person appointed on an objective basis according to specified requirements. After specific time intervals of use, eg. 0, 0.5, 1, 2, 3, 5 and 10 minutes, the content of CBD was measured in the remaining solid dosage residue. The solid dosage form was subject to triple measurements for each of the 8 test persons, giving a total of 24 measurements for each sample. An average of the 24 measurements was calculated and the weight % release was calculated based on the original content of CBD in the sample. The content of CBD was measured in the remaining solid dosage form residue, if still present.

The solid dosage form was weighted and placed in the mouth, and the test persons were instructed to place and use the solid dosage form as intended. For chewing gum, the test persons were instructed to chew the sample at a frequency of 60 chews per minute. For lozenges the test persons were instructed to place the sample between the tongue and the palate, and then the solid dosage form was sucked and turned every 0.5 minute. Once the desired test time was achieved (0.5, 1, 2, 3, 5 and 10 min.), the solid dosage form was taken out and weighed directly into a measuring glass to be used for analysis of CBD content. An in vivo dissolution profile was obtained by analyzing the content of CBD in the solid dosage form at different dissolution times.

This test was made to tablets, chewing gums, and lozenges. Also, this test was made to other cannabinoids, including THC.

Example 13

In Vitro Testing of Release in Solid Dosage Forms

A sample solid dosage form was tested. After specific time intervals of use, eg 0, 0.5, 1, 2, 3, 5 and 10 minutes, the content of CBD was measured in the remaining solid dosage residue. The solid dosage form was subject to triple measurements. An average of the measurements was calculated and the weight % release was calculated based on the original content of CBD in the sample. The content of CBD was measured in the remaining solid dosage form residue, if still present.

The solid dosage form was weighted. Then 25 ml of phosphate buffer was added into a 50 ml measuring tube with screw cap. The solid dosage form was added to the tube. The tube was fixed horizontally on a shaking table. After shaking, the solid dosage form was analyzed for content of CBD. An in vitro profile was obtained by analyzing the content of the CBD in the solid dosage at different dissolution times.

This test was made to tablets, chewing gum, and lozenges. Also, this test was made to other cannabinoids, including THC.

Example 14

CBD Delivered to the Oral Mucosa from Solid Dosage Forms

A sample was used as intended for 1 minute by a test panel of 8 test persons. The test person was a healthy person appointed on an objective basis according to specified requirements. Test subject abstains from eating and drinking at least 30 minutes before initiation of any test. The test person was not allowed to swallow during the procedure. The solid dosage form was weighted and placed in the mouth, and the test persons were instructed to place and use the solid dosage form as intended. For chewing gum, the test persons were instructed to chew the sample at a frequency of 60 chews per minute. For lozenges the test persons were instructed to place the sample between the tongue and the palate, and then the solid dosage form was sucked and turned every 10 seconds. After one minute, saliva was obtained from the test person and collected in a vessel for later analysis. In tests for 2 minutes release, the same procedure was followed until 2 minutes where the last saliva sample was collected and added to the same vessel for aggregated analysis. The aggregated saliva sample was collected after 2 minutes, and the content of CBD was measured in the saliva. The content of CBD was also measured in the remaining residue. The residue, if still present, was positioned in a flask, weighted, and analyzed. The residue, if still present, and saliva were subject to 3 triple measurements for each of the 8 test persons, giving a total of 24 measurement for each sample. An average of the 24 measurements was then calculated. By comparing the amount of CBD in the residue and the amount of CBD in the saliva with the amount of CBD in the solid dosage form before use, the amount of CBD delivered to the oral mucosa could be estimated.

This test was made to tablets, chewing gum, and lozenges. Also, this test was made to other cannabinoids, including THC.

Example 15

Sensoric Evaluation Test Set-Up of Solid Dosage Forms

In addition to release measurements, either in vivo or in vitro, sensoric tests were performed to reveal very important characteristics and properties of the solid dosage form. These sensoric parameters are important as indicators of the structure of the solid dosage form composition. The structure is the underlying guidance as to how the solid dosage form resembles the structure of a comparative solid dosage form, which is set as the standard in the test series, i.e. the solid dosage forms are compared to each other in the test series of preferably 5 samples. The test set-up was composed of 8 test persons in a test panel. All of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent, i.e. "+++++" means that the solid dosage form was excellent compared to the standard, "+++" means that the solid dosage form was comparable to the standard and "+" means that the solid dosage form was very far from comparable to the standard. "0" indicated that it was not tested.

Four different parameters were tested in a test panel:

| Friability | Flavor | Sweetness | Off-notes |
|---|---|---|---|

"Texture"—the general impression of the solid dosage form when placed in the mouth with respect to elements such as hardness, roughness and a smoothness.

"Friability"—the impression of the solid dosage form when placed in the mouth and intended use is initiated. For instance, a very hard and viscous structure gave a very low rating and a very brittle structure also gave a very low rating.

"Flavor"—the overall impression of the solid dosage form during intended use with respect to flavor. For instance, a very low flavor experience gave a very low rating and a too high flavor experience that was not comparable to the standard also gave a very low rating.

"Sweetness"—the overall impression of the taste of the solid dosage form during intended use with respect to sweetness. For instance, if the sweetness was decreasing rapidly, a very low rating was given and if the sweetness was too high giving an uncomfortable feeling, a very low rating was also given.

"Off-notes"—the overall impression of the off-note from the one or more cannabinoids in the composition during intended use. For instance, if off-notes (grass, bitter notes, irritation in the throat) were experienced in the throat, a low rating was given and if other uncomfortable sensations was experienced, a low rating was also given.

Example 16

Results on Content Uniformity in Powder Premixtures

The procedures of Example 11A was used for the powder premixes (Powder Premix Samples) above and the results are shown in the table below. The result of content uniformity for a sample is provided as a single value obtained as the relative standard deviation (RSD) of CBD content of multiple samples taken at the end of the premix preparation procedures.

TABLE 30

Content uniformity of powder premixtures with Hydrogenated Vegetable Oil (HVO)-HVO added to isolated CBD and sweetener.

| Powder Premix Sample no. | Example | Content uniformity (RSD) |
|---|---|---|
| 100 | Example 1 | 1.1% |
| 101 | Example 1 | 1.2% |
| 102 | Example 1 | 1.2% |
| 103 | Example 1 | 1.5% |
| 104 | Example 1 | 1.7% |

TABLE 31

Content uniformity of powder premixtures with Hydrogenated Vegetable Oil (HVO)-HVO added to isolated CBD and sweetener.

| Powder Premix Sample no. | Example | Content uniformity (RSD) |
|---|---|---|
| 110 | Example 1 | 1.3% |
| 111 | Example 1 | 1.3% |
| 112 | Example 1 | 1.2% |
| 113 | Example 1 | 1.2% |
| 114 | Example 1 | 1.1% |

TABLE 32

Content uniformity of powder premixtures with Hydrogenated Vegetable Oil (HVO) (preheated)- HVO added to isolated CBD and sweetener.

| Powder Premix Sample no. | Example | Content uniformity (RSD) |
|---|---|---|
| 120 | Example 1 | 1.3% |
| 121 | Example 1 | 1.1% |
| 122 | Example 1 | 1.2% |
| 123 | Example 1 | 0.9% |
| 124 | Example 1 | 1.2% |

TABLE 33

Content uniformity of powder premixtures with Miglyol- Miglyol added to isolated CBD and sweetener.

| Powder Premix Sample no. | Example | Content uniformity (RSD) |
|---|---|---|
| 200 | Example 2 | 1.1% |
| 201 | Example 2 | 1.2% |
| 202 | Example 2 | 1.1% |
| 203 | Example 2 | 1.3% |
| 204 | Example 2 | 1.5% |

TABLE 34

Content uniformity of powder premixtures with Miglyol- Miglyol added to isolated CBD and sweetener.

| Powder Premix Sample no. | Example | Content uniformity (RSD) |
|---|---|---|
| 210 | Example 2 | 1.1% |
| 211 | Example 2 | 1.1% |
| 212 | Example 2 | 1.1% |
| 213 | Example 2 | 1.0% |
| 214 | Example 2 | 1.0% |

TABLE 35

Content uniformity of powder premixtures with Miglyol- Miglyol added to isolated CBD and sweetener.

| Powder Premix Sample no. | Example | Content uniformity (RSD) |
|---|---|---|
| 220 | Example 2 | 1.1% |
| 221 | Example 2 | 1.2% |
| 222 | Example 2 | 1.1% |
| 223 | Example 2 | 1.0% |

TABLE 35

Content uniformity of powder premixtures with Miglyol-Miglyol added to isolated CBD and sweetener.

| Powder Premix Sample no. | Example | Content uniformity (RSD) |
|---|---|---|
| 230 | Example 2 | 1.2% |
| 231 | Example 2 | 1.1% |
| 232 | Example 2 | 1.1% |
| 233 | Example 2 | 1.2% |
| 234 | Example 2 | 1.1% |

TABLE 36

Content uniformity of powder premixtures with Hydrogenated Vegetable Oil (HVO)-HVO added to isolated CBD in high load and sweetener.

| Powder Premix Sample no. | Example | Content uniformity (RSD) |
|---|---|---|
| 300 | Example 3 | 2.2% |
| 301 | Example 3 | 2.6% |
| 302 | Example 3 | 2.8% |
| 303 | Example 3 | 3.0% |
| 304 | Example 3 | 3.3% |

TABLE 37

Content uniformity of powder premixtures with Hydrogenated Vegetable Oil (HVO)-—HVO added to isolated CBD in high load and sweetener.

| Powder Premix Sample no. | Example | Content uniformity (RSD) |
|---|---|---|
| 310 | Example 3 | 2.9% |
| 311 | Example 3 | 2.9% |
| 312 | Example 3 | 2.8% |
| 313 | Example 3 | 2.6% |
| 314 | Example 3 | 2.6% |

TABLE 38

Content uniformity of powder premixtures with Hydrogenated Vegetable Oil (HVO)-—HVO added to isolated CBD in high load and sweetener.

| Powder Premix Sample no. | Example | Content uniformity (RSD) |
|---|---|---|
| 320 | Example 3 | 2.8% |
| 321 | Example 3 | 2.7% |
| 322 | Example 3 | 2.8% |
| 323 | Example 3 | 2.6% |
| 324 | Example 3 | 2.9% |

TABLE 39

Content uniformity of powder premixtures with Hydrogenated Vegetable Oil (HVO)-—CBD/HVO mixture added to sweetener.

| Powder Premix Sample no. | Example | Content uniformity (RSD) |
|---|---|---|
| 400 | Example 4 | 2.6% |
| 401 | Example 4 | 2.7% |
| 402 | Example 4 | 2.7% |
| 403 | Example 4 | 2.8% |
| 404 | Example 4 | 2.8% |

TABLE 40

Content uniformity of powder premixtures with Hydrogenated Vegetable Oil (HVO)-—CBD/HVO mixture added to sweetener.

| Powder Premix Sample no. | Example | Content uniformity (RSD) |
|---|---|---|
| 410 | Example 4 | 2.7% |
| 411 | Example 4 | 2.8% |
| 412 | Example 4 | 2.7% |
| 413 | Example 4 | 2.5% |
| 414 | Example 4 | 2.6% |

TABLE 41

Content uniformity of powder premixtures with Hydrogenated Vegetable Oil (HVO)-—CBD/HVO mixture added to sweetener.

| Powder Premix Sample no. | Example | Content uniformity (RSD) |
|---|---|---|
| 420 | Example 4 | 2.6% |
| 421 | Example 4 | 2.8% |
| 422 | Example 4 | 2.7% |
| 423 | Example 4 | 2.5% |
| 424 | Example 4 | 2.7% |

TABLE 42

Content uniformity of powder premixtures with Miglyol-—CBD/Miglyol mixture added to sweetener.

| Powder Premix Sample no. | Example | Content uniformity (RSD) |
|---|---|---|
| 500 | Example 5 | 2.5% |
| 501 | Example 5 | 2.6% |
| 502 | Example 5 | 2.6% |
| 503 | Example 5 | 2.7% |
| 504 | Example 5 | 2.9% |

TABLE 43

Content uniformity of powder premixtures with Miglyol-—CBD/Miglyol mixture added to sweetener.

| Powder Premix Sample no. | Example | Content uniformity (RSD) |
|---|---|---|
| 510 | Example 5 | 2.7% |
| 511 | Example 5 | 2.8% |
| 512 | Example 5 | 2.6% |
| 513 | Example 5 | 2.6% |
| 514 | Example 5 | 2.6% |

TABLE 44

Content uniformity of powder premixtures with Miglyol-—CBD/Miglyol mixture added to sweetener.

| Powder Premix Sample no. | Example | Content uniformity (RSD) |
|---|---|---|
| 520 | Example 5 | 2.7% |
| 521 | Example 5 | 2.7% |
| 522 | Example 5 | 2.6% |
| 523 | Example 5 | 2.5% |
| 524 | Example 5 | 2.6% |

TABLE 45

Content uniformity of comparative samples—
without triglycerides lipids.

| Powder Premix Sample no. | Example | Content uniformity (RSD) |
|---|---|---|
| 600 | Example 6 | 4.2% |
| 601 | Example 6 | 4.2% |
| 602 | Example 6 | 4.3% |
| 603 | Example 6 | 4.3% |
| 604 | Example 6 | 4.5% |

TABLE 46

Content uniformity of powder premixtures with Miglyol
(not preheated)—mixture added to sweetener.

| Powder Premix Sample no. | Example | Content uniformity (RSD) |
|---|---|---|
| 610 | Example 6 | 4.1% |
| 611 | Example 6 | 4.0% |
| 612 | Example 6 | 4.0% |
| 613 | Example 6 | 3.9% |
| 614 | Example 6 | 3.9% |

TABLE 47

Content uniformity of powder premixtures with Miglyol
(not preheated)—mixture added to sweetener.

| Powder Premix Sample no. | Example | Content uniformity (RSD) |
|---|---|---|
| 620 | Example 6 | 4.2% |
| 621 | Example 6 | 4.1% |
| 622 | Example 6 | 4.3% |
| 623 | Example 6 | 4.4% |
| 624 | Example 6 | 4.4% |

Example 17

Results on Content Uniformity in Powder Blends and Solid Dosage Forms

The procedures of Example 11A was used for powder blends (Powder Blends) which are powder premixes (Powder Premix Samples) with additional ingredients as outlined in the formulations of the oral dosage forms. These powder blends were formed into the solid dosage forms. The procedure of Example 11B was used for the solid dosage forms. The results are shown in the tables below.

The result of content uniformity (CU) for a sample is provided as a single value obtained as the relative standard deviation (RSD) of CBD content of multiple samples taken at the end of the preparation procedures. If individual samples have been collected at different stages of a tableting process (eg. start, middle, end) then content uniformity is determined by analysis of pooled samples from the different process stages.

TABLE 48

Based on the procedure in Example 11B

| Powder Premix Sample No | Solid dosage form | Powder Blend CU (RSD) | Solid dosage form CU (RSD) |
|---|---|---|---|
| 102 | Example 7 (Table 20) | 2.3% | 1.5% |
| 202 | Example 7 (Table 21) | 2.1% | 1.6% |

TABLE 49

Based on the procedure in Example 11B

| Powder Premix Sample No | Solid dosage form | Powder Blend CU (RSD) | Solid dosage form CU (RSD) |
|---|---|---|---|
| 312 | Example 8 (Table 23) | 1.7% | 1.4% |
| 322 | Example 8 (Table 24) | 1.6% | 1.0% |

TABLE 50

Based on the procedure in Example 11B

| Powder Premix Sample No | Solid dosage form | Powder Blend CU (RSD) | Solid dosage form CU (RSD) |
|---|---|---|---|
| 422 | Example 9 (Table 25) | 2.8% | 1.0% |
| 502 | Example 9 (Table 26) | 3.0% | 1.2% |

TABLE 51

Based on the procedure in Example 11B

| Powder Premix Sample No | Solid dosage form | Powder Blend CU (RSD) | Solid dosage form CU (RSD) |
|---|---|---|---|
| 602 | Example 10 (Table 27) | 4.8% | 6.4% |
| 610 | Example 10 (Table 28) | 5.7% | 6.1% |
| 622 | Example 10 (Table 29) | 7.7% | 6.5% |

Example 18

Results on Content Uniformity in Further Powder Premixtures and Powder Blends

The procedures of Example 11A was also made on further powder premixtures and powder blends used in different application forms. For instance, the powder provided in the examples above was applied in pouches, sachets, and flowpacks where similar good results for content uniformity were seen.

Example 19

Results on Content Uniformity in Further Solid Dosage Forms

The procedures of Example 11B was also made on further solid dosage forms. Similar good results were seen for tablets without gum base, FDT tablets, chewing gums, and lozenges.

The invention claimed is:

1. A method of producing a powder premixture for oral administration of cannabinoids, the method comprising the steps of:

i) providing a cannabinoid powder composition comprising one or more isolated cannabinoids in an amount of at least 2% by weight of the powder premixture;

a lipid composition comprising one or more triglycerides in an amount of at least 1.0% by weight of the powder premixture; and a sweetener powder composition comprising one or more sweeteners, wherein the weight ratio between the one or more triglycerides and the one or more sweeteners is in the range of 1:50 to 1:4, and ii) adding the one or more isolated cannabinoids in the sweetener powder composition before admixture with the one or more triglycerides.

2. The method according to claim 1, wherein the one or more triglycerides is selected from one or more C4 to C14 triglycerides.

3. The method according to claim 1, wherein the one or more triglycerides is selected from one or more C6 to C12 triglycerides.

4. The method according to claim 1, wherein the one or more triglycerides comprises a partially hydrogenated vegetable oil or a fully hydrogenated vegetable oil.

5. The method according to claim 1, wherein the one or more triglycerides is selected from triglycerides being liquid at or above 0 Degree Celsius.

6. The method according to claim 1, wherein the one or more triglycerides is a blend of a number of triglycerides.

7. The method according to claim 1, wherein the one or more triglycerides is heated to a temperature above ambient temperature before being added in the premixture.

8. The method according to claim 1, wherein the one or more triglycerides is heated to a temperature of 50 to 80 Degree Celsius before being added in the premixture.

9. The method according to claim 1, wherein the one or more triglycerides comprises caprylic acid in an amount of 50 to 80% by weight.

10. The method according to claim 1, wherein the one or more sweeteners is present in an amount of at least 50% by weight of the powder premixture.

11. The method according to claim 1, wherein the one or more sweeteners comprises one or more sugar alcohols selected from the group consisting of sorbitol, xylitol, maltitol, isomalt, mannitol, erythritol, lactitol, and combinations thereof.

12. The method according to claim 1, wherein the weight ratio between the one or more triglycerides and the one or more isolated cannabinoids is in the range of 1:40 to 1:1.

13. The method according to claim 1, wherein the one or more isolated cannabinoids is present in an amount of at least 5% by weight of the powder premixture.

14. The method according to claim 1, wherein the one or more isolated cannabinoids is selected from the group consisting of cannabidiol (CBD), cannabidiolic acid (CBDA), cannabidivarin (CBDV), and combinations thereof.

15. The method according to claim 1, wherein the one or more isolated cannabinoids is selected from the group consisting of tetrahydrocannabinol (THC), tetrahydrocannabinolic acid (THCA), tetrahydrocannabivarin (THCV), and combinations thereof.

16. The method according to claim 1, wherein the one or more isolated cannabinoids is present in a purity of at least 90% (w/w).

17. The method according to claim 1, wherein the premixture is a ready-to-use premixture.

18. The method according to claim 1, wherein the method comprises a step iii) of combining the premixture of step ii) in an amount of 10-99.9% by weight with further ingredients.

19. A method of producing a powder premixture for oral administration of cannabinoids, the method comprising the steps of:

i) providing a cannabinoid powder composition comprising one or more isolated cannabinoids in an amount of at least 2% by weight of the powder premixture;

a lipid composition consisting of one or more triglycerides in an amount of at least 1.0% by weight of the powder premixture; and a sweetener powder composition comprising one or more sweeteners, wherein the weight ratio between the one or more triglycerides and the one or more sweeteners is in the range of 1:50 to 1:4, and ii) dissolving the one or more isolated cannabinoids in the one or more triglycerides before admixture with the sweetener powder composition.

20. The method according to claim 19, wherein the method comprises a step iii) of combining the premixture of step ii) in an amount of 10-99.9% by weight with further ingredients.

21. A method of producing a powder premixture for oral administration of cannabinoids, the method comprising the steps of:

i) providing a cannabinoid powder composition comprising one or more isolated cannabinoids in an amount of at least 2% by weight of the powder premixture;

a lipid composition consisting of one or more triglycerides in an amount of at least 1.0% by weight of the powder premixture; and a sweetener powder composition comprising one or more sweeteners, wherein the weight ratio between the one or more triglycerides and the one or more sweeteners is in the range of 1:50 to 1:4, and ii) adding the one or more triglycerides in the sweetener powder composition before admixture with the one or more isolated cannabinoids.

22. The method according to claim 21, wherein the method comprises a step iii) of combining the premixture of step ii) in an amount of 10-99.9% by weight with further ingredients.

\* \* \* \* \*